(12) United States Patent
Ninomiya et al.

(10) Patent No.: US 11,351,067 B2
(45) Date of Patent: Jun. 7, 2022

(54) ABSORBENT ARTICLE AND METHOD AND DEVICE FOR MANUFACTURING ABSORBENT ARTICLE

(71) Applicant: UNICHARM Corporation, Ehime (JP)

(72) Inventors: Akihide Ninomiya, Kagawa (JP); Masaharu Tomioka, Kagawa (JP)

(73) Assignee: Unicharm Corporation, Ehime (JP)

( * ) Notice: Subject to any disclaimer, the term of this patent is extended or adjusted under 35 U.S.C. 154(b) by 348 days.

(21) Appl. No.: 16/546,541

(22) Filed: Aug. 21, 2019

(65) Prior Publication Data

US 2019/0374392 A1    Dec. 12, 2019

Related U.S. Application Data

(63) Continuation of application No. PCT/JP2017/006903, filed on Feb. 23, 2017.

(51) Int. Cl.
*A61F 13/15* (2006.01)
*A61F 13/49* (2006.01)
(Continued)

(52) U.S. Cl.
CPC .. *A61F 13/15739* (2013.01); *A61F 13/15593* (2013.01); *A61F 13/15747* (2013.01); *A61F 13/15764* (2013.01); *A61F 13/4902* (2013.01); *A61F 13/496* (2013.01); *A61F 13/49019* (2013.01); *B29C 65/741* (2013.01); *B29C 66/4722* (2013.01); *B29C 66/84* (2013.01); *A61F 2013/15869* (2013.01);
(Continued)

(58) Field of Classification Search
None
See application file for complete search history.

(56) References Cited

U.S. PATENT DOCUMENTS

2010/0076394 A1* 3/2010 Hayase ............... B29C 66/1122
604/385.29
2016/0331600 A1* 11/2016 Polidori ............ A61F 13/15593

FOREIGN PATENT DOCUMENTS

CN    101868210 A    10/2010
CN    102448418 A    5/2012
(Continued)

OTHER PUBLICATIONS

International Preliminary Report on Patentability issued in International Application No. PCT/JP2017/006903, dated Sep. 6, 2019 (7 pages).
(Continued)

*Primary Examiner* — Barbara J Musser
(74) *Attorney, Agent, or Firm* — Osha Bergman Watanabe & Burton LLP

(57) ABSTRACT

An absorbent article includes: a first sheet-like member; a second sheet-like member; an elastic member that is inserted along a lateral direction between a pair of mutually-opposing facing surfaces of the first sheet-like member; joining portions that join the pair of mutually-opposing facing surfaces and that are spaced apart in the lateral direction; and side-seal sections that are disposed at each lateral end portion of the absorbent article. The joining portions are disposed on two sides of the elastic member in a vertical direction, which intersects the lateral direction and a front-rear direction, so that the elastic member is sandwiched and pressed between the joining portions.

11 Claims, 15 Drawing Sheets

(51) Int. Cl.
  *A61F 13/496*  (2006.01)
  *B29C 65/74*   (2006.01)
  *B29C 65/00*   (2006.01)
  B29L 31/48     (2006.01)

(52) U.S. Cl.
  CPC ............... *A61F 2013/15878* (2013.01); *A61F 2013/49025* (2013.01); *A61F 2013/49031* (2013.01); *A61F 2013/49093* (2013.01); *B29K 2995/0046* (2013.01); *B29K 2995/0068* (2013.01); *B29L 2031/4878* (2013.01)

(56) References Cited

FOREIGN PATENT DOCUMENTS

| CN | 105142589 A   | 12/2015 |
| CN | 204971881 U   | 1/2016  |
| CN | 106029029 A   | 10/2016 |
| CN | 106137542 A   | 11/2016 |
| EP | 3111901 A1    | 1/2017  |
| JP | 2000-279444 A | 10/2000 |
| JP | 2001-504899 A | 4/2001  |
| JP | 2005-514244 A | 5/2005  |
| WO | 2016/181774 A1| 11/2016 |
| WO | 2016208513 A1 | 12/2016 |

OTHER PUBLICATIONS

Written Opinion of the International Searching Authority issued in corresponding International Application No. PCT/JP2017/006903 dated May 16, 2017 (4 pages).

International Search Report issued in corresponding International Application No. PCT/JP2017/006903 dated May 16, 2017 (4 pages).

Extended European Search Report issued in corresponding European Patent Application No. 17898014.0, dated Feb. 14, 2020 (7 pages).

Office Action issued in the counterpart Chinese Patent Application No. 201780087128.8, dated Apr. 12, 2021 (11 pages).

Office Action issued in the counterpart Chinese Patent Application No. 201780087128.8, dated Oct. 15, 2021 (11 pages).

* cited by examiner

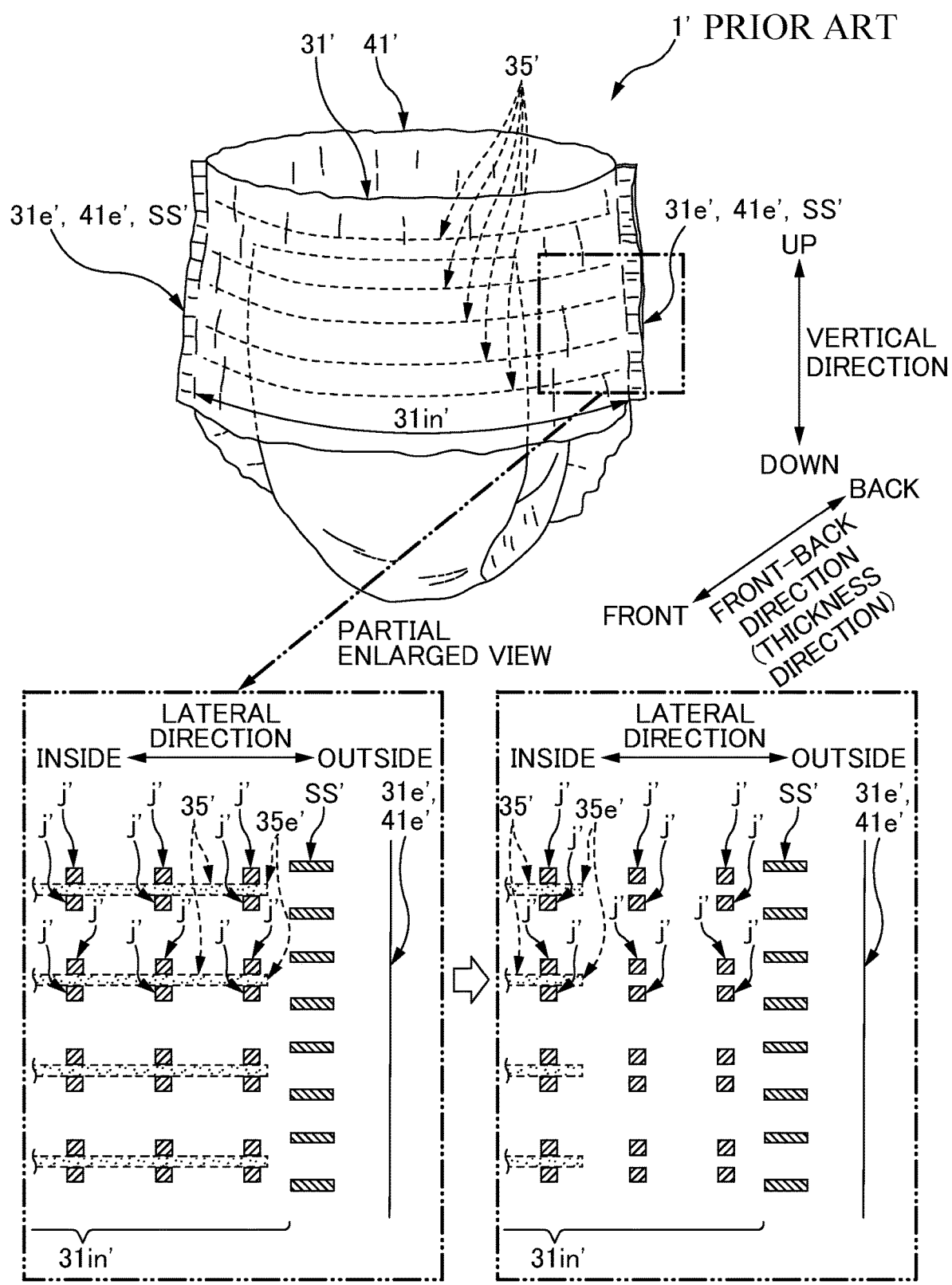

ABSORBENT ARTICLE AND METHOD AND DEVICE FOR MANUFACTURING ABSORBENT ARTICLE

TECHNICAL FIELD

The present invention relates to an absorbent article such as a disposable diaper and a method and a device for manufacturing the absorbent article.

BACKGROUND

A disposable diaper 1' shown in the schematic perspective view of FIG. 1A is a conventional example of an absorbent article that absorbs excrement such as urine. This diaper 1' includes a first sheet-like member 31' and a second sheet-like member 41' that have been given stretchability in the lateral direction by elastic members 35' attached thereto. And, the diaper 1' also includes side-seal sections SS' in end portions 31e' (41e') in the lateral direction, and in the side-seal sections SS', the two sheet-like members are welded together overlaid in the thickness direction, which intersects the lateral direction and the vertical direction.

The elastic members 35' are normally attached to the first sheet-like member 31' with use of an adhesive. However, when the elastic members 35' are attached with use of an adhesive, there is a risk that hardening of the adhesive at the outer circumferential surfaces of the elastic members 35' will impair the elasticity (i.e., stretchability) of the elastic members 35' and impair the softness of the first sheet-like member 31'. For this reason, in recent years, consideration has been given to the attachment of the elastic members 35' to the first sheet-like member 31' without using an adhesive, and the following is one example of such a method disclosed in PTL 1.

PATENT LITERATURE

[PTL 1] Japanese Unexamined Patent Application Publication (Translation of PCT Application) No. 2001-504899

FIGS. 1B and 1C are schematic plan views for describing the aforementioned method. In the enlarged view of FIG. 1C, the elastic members 35' contract in the direction of transport compared to FIG. 1B as will be described later, the direction-of-transport gaps between joining portions j' that are adjacent in the direction of transport are actually smaller than the direction-of-transport gaps between the joining portions j' in the enlarged view in FIG. 1B. But, for the sake of convenience, these gaps in FIG. 1C are shown at the same size as in FIG. 1B. The same follows for the enlarged views in FIGS. 6A and 6B that will be described later. The following describes the aforementioned method with reference to FIGS. 1B and 1C.

First, as shown in FIG. 1B, the first sheet-like-member continuous body 31a' is continuous in the direction of transport, and is transported with its direction of transport conforming to the lateral direction of the diaper 1'. Elastic-member continuous bodies 35a' are continuous in the direction of transport, and are inserted between a pair of mutually-opposing facing surfaces of the first sheet-like-member continuous body 31a' with stretched in the direction of transport.

Next, a plurality of joining portions j' for joining the pair of facing surfaces are formed at intervals in the direction of transport. At this time, the joining portions j' are formed at positions on two sides of the elastic-member continuous body 35a' with respect to a CD direction that intersects the direction of transport.

Subsequently, the first sheet-like-member continuous body 31a' is cut at cutting target positions PC' of the continuous body 31a' in the direction of transport, thus forming cutform-shaped first sheet-like members 31' having the elastic members 35' attached thereto as shown in FIG. 1C. Due to this cutting, the elastic members 35' that have been cut contract in the direction of transport and attempt to expand in the CD direction. But here, the expansion of the elastic members 35' in the CD direction is restricted by the pairs of joining portions j' located on the two sides in the CD direction, and therefore the elastic members 35' are substantially sandwiched and pressed in the CD direction by the joining portions j'. As a result, the elastic members 35' are attached to the first sheet-like member 31'.

Also, as shown in FIG. 1C, when cutting is performed at the cutting target positions PC', the second sheet-like-member continuous body 41a' has already been overlaid on the first sheet-like-member continuous body 31a', and the side-seal sections SS' have already been formed on the two sides of the cutting target positions PC' in the direction of transport.

Accordingly, after the first sheet-like members 31a' are produced by the cutting at the cutting target positions PC', each first sheet-like member 31a' is provided with the two side-seal sections SS' in the respective lateral end portions 31e'; at this time the lateral direction conforms the direction of transport.

Also, in the state of the diaper 1' shown in FIG. 1A, a portion 31in' of the first sheet-like member 31' that is laterally inward of the side-seal sections SS' on the two lateral sides comes into contact with the stomach side of the wearer's torso. For this reason, the inward portion 31in' is given stretchability in the lateral direction by the elastic members 35'.

Note that when this diaper 1 is to be used, the inward portion 31in' stretches in the lateral direction, and the elastic members 35' also stretch in the lateral direction at that time. Accordingly, due to this stretching, the elastic members 35' contract in the vertical direction (same direction as the CD direction) that intersects the lateral direction, and as a result, the compression of the elastic members 35' between pairs of the joining portions j' is relaxed. If this relaxation occurs in lateral end portions 35e' of the elastic members 35', there is a risk that the end portions 35e' will successively detach from the pairs of joining portions j' arranged in the lateral direction, and that, as a result, the elastic members 35' will detach from the pairs of joining portions j' over a wide range in the inward portion 31in' as shown in the change from the left-side state to the right-side state in the partial enlarged views in FIG. 1A.

In view of this, as shown in FIG. 1D, portions 31out' of the first sheet-like member 31' that are laterally outward of the side-seal sections SS' are portions that are not stretched in the lateral direction when the diaper 1' is used. For this reason, if the above-described pairs of joining portions j' are provided in the outward portions 31out', it is thought to be possible to suppress the case where the end portions 35e' of the elastic members 35' detach from the pairs of joining portions j' in the first sheet-like member 31' when the diaper 1' is used.

SUMMARY

One or more embodiments of the present invention suppress the detachment of the lateral end portions of an elastic member from pairs of joining portions of a first sheet-like member of an absorbent article when the first sheet-like member stretches in the lateral direction during use of the absorbent article.

According to one or more embodiments, a method for manufacturing an absorbent article is provided. The absorbent article including a first sheet-like member, a second sheet-like member, an elastic member, and a side-seal section, the elastic member being attached to the first sheet-like member, the first sheet-like member having been a stretchability in a lateral direction by the elastic member, the side-seal section being provided in each lateral end portion of the absorbent article, the first sheet-like member and the second sheet-like member being overlaid in a thickness direction and welded together in the side-seal section, and the thickness direction being a direction that intersects the lateral direction. The method includes:

an arranging step of arranging a plurality of elastic-member continuous bodies between a pair of mutually-opposing facing surfaces of a first sheet-like-member continuous body that is being transported,
a direction of transport of the first sheet-like-member continuous body conforming to the lateral direction,
the plurality of elastic-member continuous bodies being continuous in the direction of transport,
the first sheet-like-member continuous body being continuous in the direction of transport,
the plurality of elastic-member continuous bodies being in a stretched state in the direction of transport;
a joining-portion forming step of forming a plurality of joining portions spacing in the direction of transport,
the joining portions joining the pair of facing surfaces of the first sheet-like-member continuous body to each other,
the joining-portion forming step including forming the plurality of joining portions on two sides of the elastic-member continuous bodies in a CD direction while maintaining the elastic-member continuous bodies in a state of being stretched in the direction of transport,
the CD direction intersecting the direction of transport and the thickness direction,
the joining portions being formed so that, by direction-of-transport contraction and CD-direction expansion of the elastic member after a cutting step, the elastic member is sandwiched and pressed in the CD direction by the joining portions on the two sides, being attached to the first sheet-like member,
the joining portions being formed so that a portion of at least one of the joining portions is located in the direction of transport between the side-seal section and each of cutting target positions in a view of the first sheet-like-member continuous body in the thickness direction,
the cutting target positions being set at a predetermined pitch in the direction of transport;
an overlaying step of overlaying, in the thickness direction, a second sheet-like-member continuous body on the first sheet-like-member continuous body in which the joining portions have been formed,
the second sheet-like-member continuous body being continuous in the direction of transport;
a side-seal-section forming step of forming the side-seal section on each of two sides of each of the cutting target positions in the direction of transport,
the first sheet-like-member continuous body and the second sheet-like-member continuous body that have been overlaid on each other in the thickness direction being welded together in the side-seal section; and
the cutting step of producing the absorbent article that has the elastic member, the first sheet-like member, and the second sheet-like member,
the cutting step being performed after the side-seal-section forming step and by cutting the first sheet-like-member continuous body, the elastic-member continuous bodies, and the second sheet-like-member continuous body at each of the cutting target positions.

Further, according to one or more embodiments, a device for manufacturing an absorbent article is provided. The absorbent article including a first sheet-like member, a second sheet-like member, an elastic member, and a side-seal section, the elastic member being attached to the first sheet-like member, the first sheet-like member having been a stretchability in a lateral direction by the elastic member, the side-seal section being provided in each lateral end portion of the absorbent article, the first sheet-like member and the second sheet-like member being overlaid in a thickness direction and welded together in the side-seal section, and the thickness direction being a direction that intersects the lateral direction. The device includes:

an arranging device configured to arrange a plurality of elastic-member continuous bodies between a pair of mutually-opposing facing surfaces of a first sheet-like-member continuous body that is being transported,
a direction of transport of the first sheet-like-member continuous body conforming to the lateral direction,
the plurality of elastic-member continuous bodies being continuous in the direction of transport,
the first sheet-like-member continuous body being continuous in the direction of transport,
the plurality of elastic-member continuous bodies being in a stretched state in the direction of transport;
a joining-portion forming device configured to form a plurality of joining portions spacing in the direction of transport,
the joining portions joining the pair of facing surfaces of the first sheet-like-member continuous body to each other,
the joining-portion forming device forming the plurality of joining portions on two sides of the elastic-member continuous bodies in a CD direction while maintaining the elastic-member continuous bodies in a state of being stretched in the direction of transport,
the CD direction intersecting the direction of transport and the thickness direction,
the joining portions being formed so that, by direction-of-transport contraction and CD-direction expansion of the elastic member at a position downstream in the direction of transport with respect to a cutting device, the elastic member is sandwiched and pressed in the CD direction by the joining portions on the two sides, being attached to the first sheet-like member,
the joining portions being formed so that a portion of at least one of the joining portions is located in the direction of transport between the side-seal section and each of cutting target positions,
the cutting target positions being set at a predetermined pitch in the direction of transport;
an overlaying device configured to overlay, in the thickness direction, a second sheet-like-member continuous body on the first sheet-like-member continuous body in which the joining portions have been formed,
the second sheet-like-member continuous body being continuous in the direction of transport;

a side-seal-section forming device configured to form the side-seal section on each of two sides of each of the cutting target positions in the direction of transport, the first sheet-like-member continuous body and the second sheet-like-member continuous body that have been overlaid on each other in the thickness direction being welded together in the side-seal section; and the cutting device configured to produce the absorbent article that has the elastic member, the first sheet-like member, and the second sheet-like member, at a position downstream in the direction of transport with respect to the side-seal-section forming device, the cutting device being performed by cutting the first sheet-like-member continuous body, the elastic-member continuous bodies, and the second sheet-like-member continuous body at each of the cutting target positions.

Further, according to one or more embodiments, an absorbent article includes:

a first sheet-like member;

a second sheet-like member;

an elastic member that is inserted along a lateral direction between a pair of mutually-opposing facing surfaces of the first sheet-like member;

a plurality of joining portions that for joining together the pair of facing surfaces and that are arranged spacing in the lateral direction, the joining portions being formed on two sides of the elastic member in a vertical direction so that the elastic member is sandwiched and pressed between the joining portions on the two sides, the vertical direction being a direction that intersects the lateral direction and a front-rear direction, the front-rear direction being a direction that intersects the lateral direction; and a side-seal section that is provided in each lateral end portion, a portion of at least one of the joining portions being provided at a position laterally outward of the side-seal section in the first sheet-like member in a view of the first sheet-like member in the thickness direction, the first sheet-like member and the second sheet-like member being overlaid in the front-rear direction and welded in the side-seal section.

Features of embodiments of the present invention other than the above will become clear by reading the description of the present specification with reference to the accompanying drawings.

According to one or more embodiments of the present invention, it is possible to suppress the detachment of a lateral end portion of an elastic member from a pair of joining portions of a first sheet-like member of an absorbent article when the first sheet-like member stretches in the lateral direction during use of the absorbent article.

BRIEF DESCRIPTION OF THE DRAWINGS

FIG. 1A is a schematic perspective view of a disposable diaper 1' as one example of an absorbent article.

DETAILED DESCRIPTION

Figure 1B:
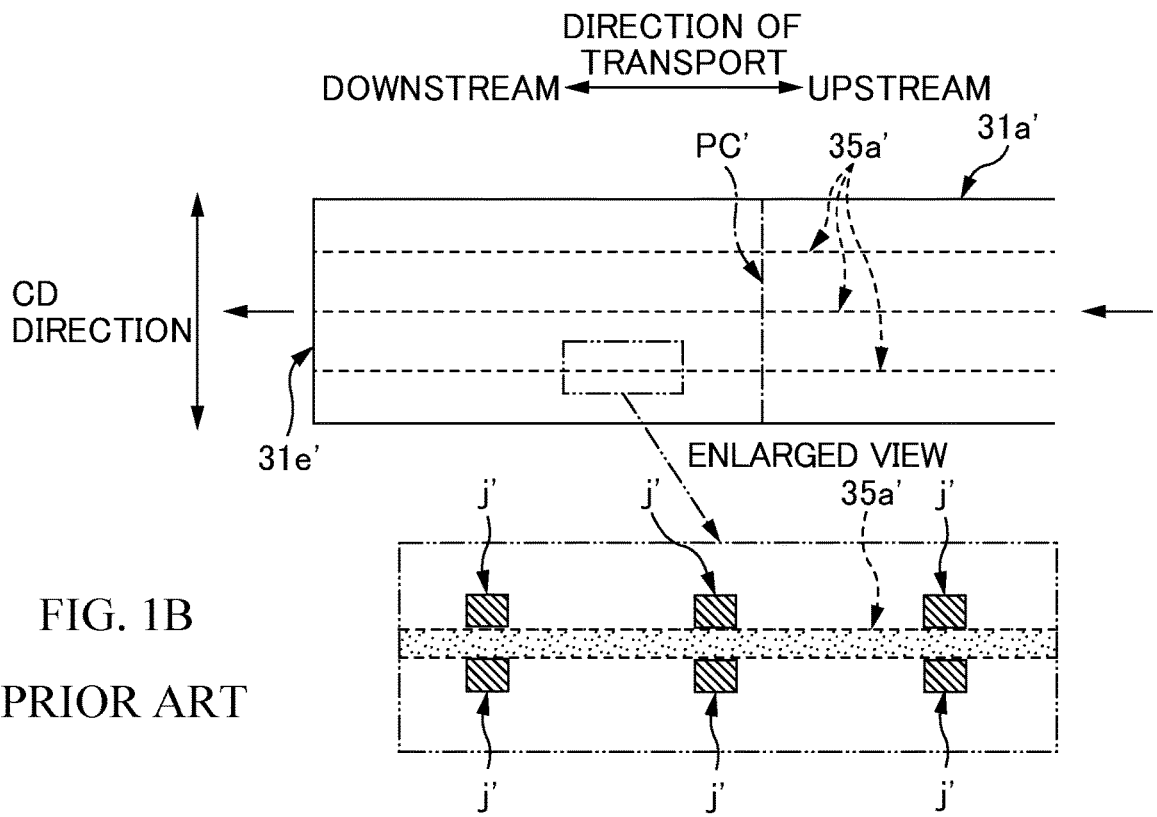
FIG. 1B is a diagram illustrating a method for attaching elastic members 35' to a first sheet-like member 31' pertaining to the diaper 1' without using an adhesive.
Figure 1C:
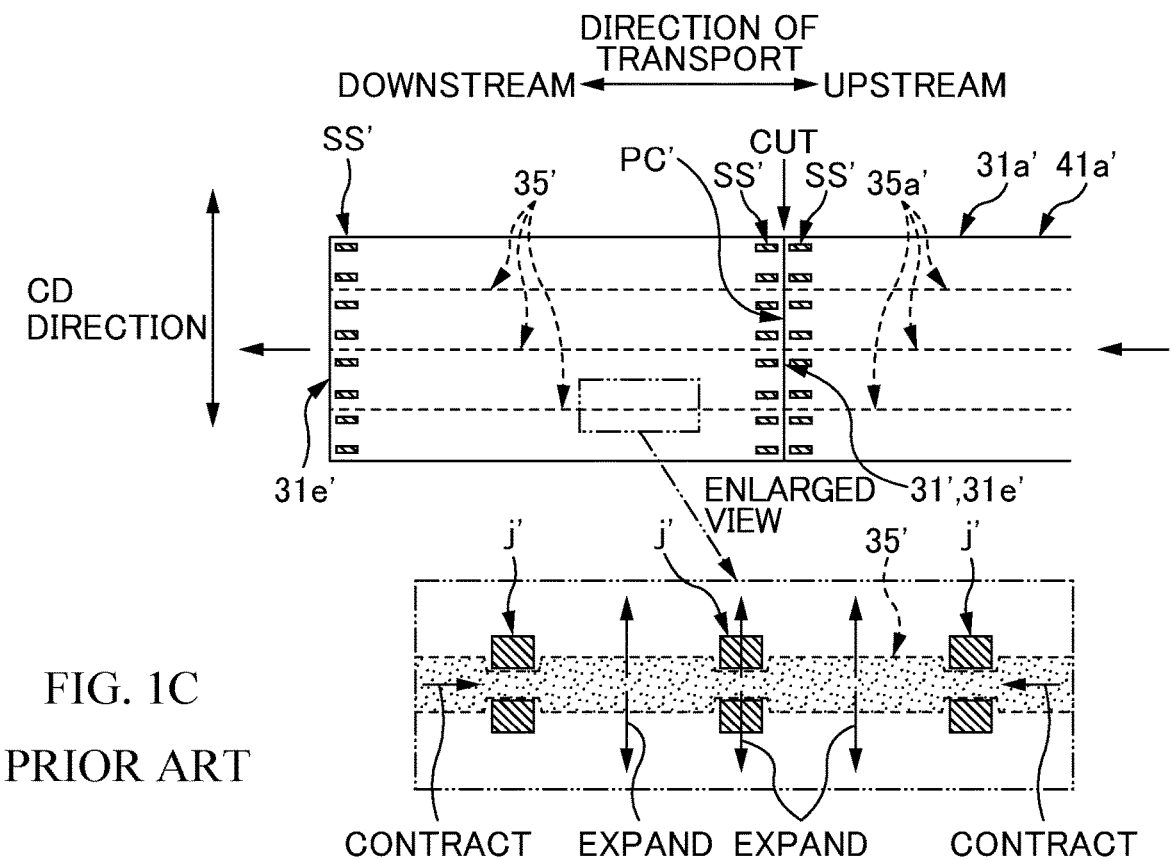
FIG. 1C is a diagram illustrating the above method.
Figure 1D:
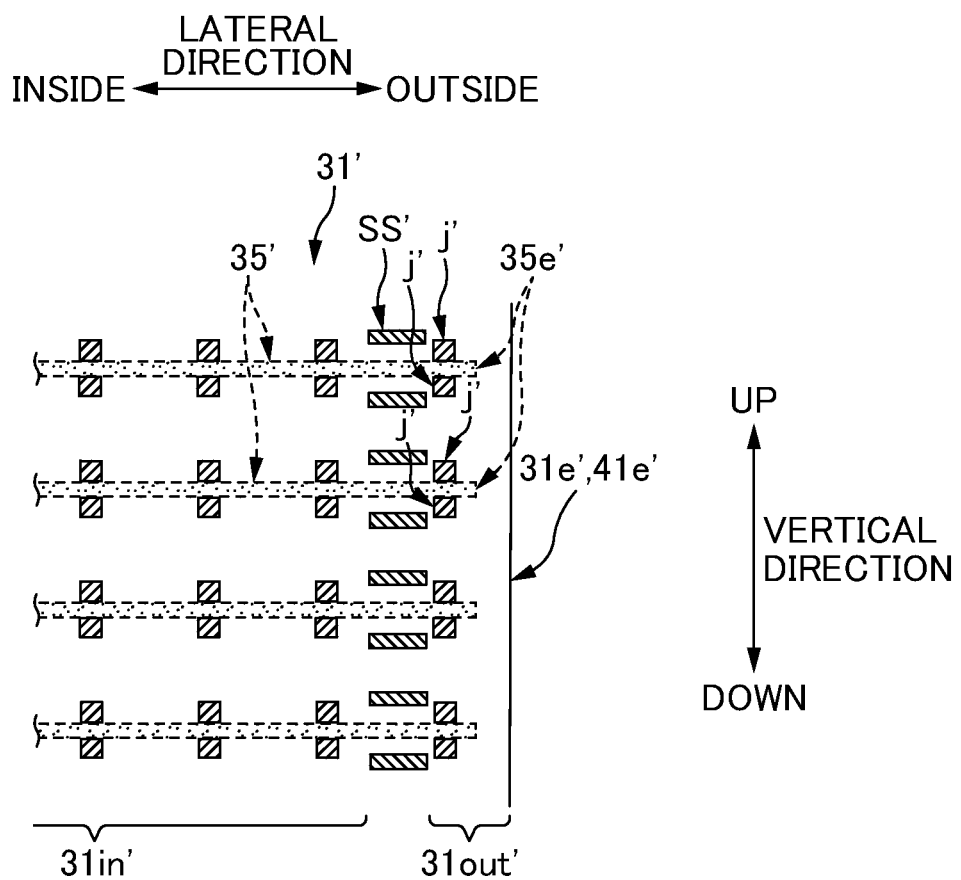
FIG. 1D is an illustrative diagram of a means for preventing detachment of end portions 35e' of elastic members 35' from pairs of joining portions j', which can occur in the above method of FIG. 1C.

At least the following matters will become clear with the description of this specification and the attached drawings.

A method for manufacturing an absorbent article, the absorbent article including a first sheet-like member, a second sheet-like member, an elastic member, and a side-seal section, the elastic member being attached to the first sheet-like member, the first sheet-like member having been a stretchability in a lateral direction by the elastic member, the side-seal section being provided in each lateral end portion of the absorbent article, the first sheet-like member and the second sheet-like member being overlaid in a thickness direction and welded together in the side-seal section, the thickness direction being a direction that intersects the lateral direction, the method including:

an arranging step of arranging a plurality of elastic-member continuous bodies between a pair of mutually-opposing facing surfaces of a first sheet-like-member continuous body that is being transported, a direction of transport of the first sheet-like-member continuous body conforming to the lateral direction, the plurality of elastic-member continuous bodies being continuous in the direction of transport, the first sheet-like-member continuous body being continuous in the direction of transport, the plurality of elastic-member continuous bodies being in a stretched state in the direction of transport;

a joining-portion forming step of forming a plurality of joining portions spacing in the direction of transport, the joining portions joining the pair of facing surfaces of the first sheet-like-member continuous body to each other, the joining-portion forming step including forming the plurality of joining portions on two sides of the elastic-member continuous bodies in a CD direction while maintaining the elastic-member continuous bodies in a state of being stretched in the direction of transport, the CD direction intersecting the direction of transport and the thickness direction, the joining portions being formed so that, by direction-of-transport contraction and CD-direction expansion of the elastic member after a cutting step, the elastic member is sandwiched and pressed in the CD direction by the joining portions on the two sides, being attached to the first sheet-like member, the joining portions being formed so that a portion of at least one of the joining portions is located in the direction of transport between the side-seal section and each of cutting target positions in a view of the first sheet-like-member continuous body in the thickness direction, the cutting target positions being set at a predetermined pitch in the direction of transport;

an overlaying step of overlaying, in the thickness direction, a second sheet-like-member continuous body on the first sheet-like-member continuous body in which the joining portions have been formed, the second sheet-like-member continuous body being continuous in the direction of transport;

a side-seal-section forming step of forming the side-seal section on each of two sides of each of the cutting target positions in the direction of transport, the first sheet-like-member continuous body and the second sheet-like-member continuous body that have been overlaid on each other in the thickness direction being welded together in the side-seal section; and the cutting step of producing the absorbent article that has the elastic member, the first sheet-like member, and the second sheet-like member, the cutting step being performed after the side-seal-section forming step and by cutting the first sheet-like-member continuous body, the elastic-member continuous bodies, and the second sheet-like-member continuous body at each of the cutting target positions.

According to this method for manufacturing an absorbent article, a portion of at least one of the joining portions is located in the direction of transport at a position between the side-seal section and the cutting target position. This position is located in a portion of the first sheet-like member of the absorbent article that is located laterally outward of the side-seal section, that is to say a portion that is not stretched in the lateral direction when the absorbent article is used. For this reason, the end portions of the elastic member can be prevented from stretching during usage of the absorbent article, and as a result, it is possible to suppress detachment that can occur if the end portions of the elastic members stretch, that is to say the relaxation of the pressed state of the end portions of the elastic member sandwiched between the joining portions and the detachment of the end portions from the joining portions.

In such a method for manufacturing an absorbent article, in the cutting step, the cutting is performed along each of cutting target lines that serve as the cutting target positions and that extend in the CD direction, and that concerning at least one of the joining portions whose are partially located between the side-seal section and the cutting target line, a longitudinal direction of the at least one joining portion intersects a direction in which the cutting target lines extend.

According to this method for manufacturing an absorbent article, the longitudinal direction of the at least one joining portion intersects the direction in which the cutting target line extends. It is therefore possible to raise the probability that the joining portion will be provided straddling the cutting target line in the direction of transport. Accordingly, after cutting is performed at the cutting target line, the joining portion provided straddling the cutting target line in the direction of transport can suppress cases where the pair of facing surfaces of the first sheet-like member pertaining to the absorbent article spread apart so as to form an opening, thus degrading the appearance.

In such a method for manufacturing an absorbent article, the at least one joining portion having the longitudinal direction is provided straddling the cutting target lines in the direction of transport.

According to this method for manufacturing an absorbent article, the joining portion is provided straddling the cutting target line in the direction of transport. Accordingly, after cutting is performed at the cutting target line, the joining portion can suppress cases where the pair of facing surfaces of the first sheet-like member pertaining to the absorbent article spread apart so as to form an opening, thus degrading the appearance.

In such a method for manufacturing an absorbent article, a size of a direction-of-transport space between the side-seal section and the cutting target position is greater than a direction-of-transport size of the side-seal section.

According to this method for manufacturing an absorbent article, the size of the direction-of-transport space between the side-seal section and the cutting target position is greater than the direction-of-transport size of the side-seal section. Accordingly, the former size can be more easily set larger than in the case where the size relationship is the opposite of the above-described relationship. This makes it possible to more easily ensure a relatively large distance in the direction of transport between the joining portion and the end portion of the elastic-member continuous body that will be the end portion of the elastic member. With this configuration, the elastic member can contract in the direction of transport so as to swiftly expand in the CD direction such that the elastic string can be sandwiched and pressed between the joining portions. As a result, it is possible to suppress the detachment of the end portion of the elastic member from the joining portions.

In such a method for manufacturing an absorbent article, a plurality of the elastic-member continuous bodies are arranged side-by-side in the CD direction, that when two of the joining portions that are on the two sides in the CD direction is defined as a joining portion pair, the joining portion pair is provided for each of the elastic-member continuous bodies, and that at least three of the joining portion pairs located between the side-seal section and the cutting target position are located on a straight line that intersects the direction of transport.

According to this method for manufacturing an absorbent article, at least three of the joining portion pairs are approximately aligned on a straight line. Also, wrinkles are ultimately formed in the first sheet-like member at direction-of-transport positions in the vicinity of the joining portion pairs due to direction-of-transport contraction of the elastic members. And here, given that the three joining portion pairs are approximately aligned as described above, the wrinkles will also be in a similarly aligned arrangement. Accordingly, the wrinkles can be presented in an orderly arrangement, and this makes it possible to improve the appearance of the first sheet-like member of the absorbent article.

In such a method for manufacturing an absorbent article, at least several of the joining portions are provided at a predetermined formation pitch in the direction of transport so as to span and extend in the direction of transport beyond the cutting target position and beyond the side-seal sections on the two sides of the cutting target position, and that when a portion of the first sheet-like-member continuous body that is located between the side-seal sections on the two sides of the cutting target position and in which the side-seal section is not formed is defined as a side-seal-portion-non-formation portion, the formation pitch is smaller than half of a direction-of-transport size of the side-seal-portion-non-formation portion.

According to this method for manufacturing an absorbent article, due to the above-described size relationship, a portion of at least one of the joining portions can be reliably provided at a position between the side-seal section and the cutting target position in the direction of transport.

In such a method for manufacturing an absorbent article, a second elastic member is attached to the second sheet-like member, that the second sheet-like member has been given stretchability in the lateral direction by the second elastic member, that the method further comprises:

a second arranging step of arranging a plurality of second elastic-member continuous bodies between a pair of mutually-opposing facing surfaces of the second sheet-like-member continuous body, the plurality of second elastic-member continuous bodies being continuous in the direction of transport, the plurality of second elastic-member continuous bodies being in a stretched state in the direction of transport; and a second joining-portion forming step of forming a plurality of second joining portions spacing in the direction of transport;

the second joining portions joining the pair of facing surfaces of the second sheet-like-member continuous body to each other, the second joining-portion forming step including forming the plurality of second joining portions on two sides of the second elastic-member continuous bodies in the CD direction while maintaining the second elastic-member continuous bodies in a state of being stretched in the direction of transport, the second joining portions being formed so that, by direction-of-transport contraction and CD-direction expansion of the second elastic member after the cutting step, the second elastic member is sandwiched and pressed in the CD direction by the second joining portions on the two sides, being attached to the second sheet-like member, the second joining portions being formed so that a portion of at least one of the second joining portions is located in the direction of transport between the side-seal section and each of the cutting target positions in a view of the second sheet-like-member continuous body in the thickness direction, that in the overlaying step, the second sheet-like-member continuous body in which the second joining portions have been formed is overlaid in the thickness direction on the first sheet-like-member continuous body in which the joining portions have been formed, and that in the cutting step, the absorbent article that has the elastic member, the first sheet-like member, the second elastic member, and the second sheet-like member is produced by cutting the first sheet-like-member continuous body, the elastic-member continuous bodies, the second sheet-like-member continuous body and the second elastic-member continuous bodies at each of the cutting target positions.

According to this method for manufacturing an absorbent article, the second elastic member and the second joining portions are provided in the second sheet-like member. Accordingly, stretchability in the lateral direction can be given to not only the first sheet-like member but also the second sheet-like member.

Also, a portion of at least one of the second joining portions is provided at a position between the side-seal section and the cutting target position in the second sheet-like member. Also, the elastic member is attached to the second sheet-like member by being sandwiched and pressed between the second joining portions, and this position is located in a portion of the second sheet-like member of the absorbent article that is located laterally outward of the side-seal section. In other words, this portion is a portion that is not stretched in the lateral direction when the absorbent article is used. For this reason, the end portions of the elastic member can be prevented from stretching during usage of the absorbent article, and as a result, it is possible to suppress detachment that can occur if the end portions of the elastic members stretch, that is to say the relaxation of the pressed state of the end portions of the elastic member sandwiched between the second joining portions and the detachment of the end portions from the second joining portions.

In such a method for manufacturing an absorbent article, when the joining portion that is in the first sheet-like-member continuous body and that is at least partially provided between the side-seal section and the cutting target position is defined as a first margin joining portion, and when the joining portion that is in the second sheet-like-member continuous body and that is at least partially provided between the side-seal section and the cutting target position is defined as a second margin joining portion, in the overlaying step, the first sheet-like-member continuous body and the second sheet-like-member continuous body are overlaid such that at least one of the first margin joining portions is shifted in the direction of transport or the CD direction with respect to one of a plurality of the second margin joining portions that is closest to the at least one first margin joining portion.

According to this method for manufacturing an absorbent article, at least one of the plurality of first margin joining portions is shifted in the direction of transport or the CD direction with respect to the second margin joining portion that is closest in the CD direction to the at least one first margin joining portion. Accordingly, it is possible to suppress stiffness that can occur if the first margin joining portion and the second margin joining portion are completely overlapped, that is to say the stiffness of a portion laterally outward with respect to the side-seal section of the absorbent article will vary greatly, which is likely to cause the person touching that portion to feel discomfort.

Further, a device for manufacturing an absorbent article, the absorbent article including a first sheet-like member, a second sheet-like member, an elastic member, and a side-seal section,
the elastic member being attached to the first sheet-like member,
the first sheet-like member having been a stretchability in a lateral direction by the elastic member,
the side-seal section being provided in each lateral end portion of the absorbent article,
the first sheet-like member and the second sheet-like member being overlaid in a thickness direction and welded together in the side-seal section,
the thickness direction being a direction that intersects the lateral direction,
the device including:
an arranging device configured to arrange a plurality of elastic-member continuous bodies between a pair of mutually-opposing facing surfaces of a first sheet-like-member continuous body that is being transported,
a direction of transport of the first sheet-like-member continuous body conforming to the lateral direction,
the plurality of elastic-member continuous bodies being continuous in the direction of transport,
the first sheet-like-member continuous body being continuous in the direction of transport,
the plurality of elastic-member continuous bodies being in a stretched state in the direction of transport;
a joining-portion forming device configured to form a plurality of joining portions spacing in the direction of transport,
the joining portions joining the pair of facing surfaces of the first sheet-like-member continuous body to each other,
the joining-portion forming device forming the plurality of joining portions on two sides of the elastic-member continuous bodies in a CD direction while maintaining the elastic-member continuous bodies in a state of being stretched in the direction of transport,
the CD direction intersecting the direction of transport and the thickness direction,
the joining portions being formed so that, by direction-of-transport contraction and CD-direction expansion of the elastic member at a position downstream in the direction of transport with respect to a cutting device, the elastic member is sandwiched and pressed in the CD direction by the joining portions on the two sides, being attached to the first sheet-like member,
the joining portions being formed so that a portion of at least one of the joining portions is located in the direction of transport between the side-seal section and each of cutting target positions,
the cutting target positions being set at a predetermined pitch in the direction of transport;
an overlaying device configured to overlay, in the thickness direction, a second sheet-like-member continuous body on the first sheet-like-member continuous body in which the joining portions have been formed,
the second sheet-like-member continuous body being continuous in the direction of transport;
a side-seal-section forming device configured to form the side-seal section on each of two sides of each of the cutting target positions in the direction of transport,
the first sheet-like-member continuous body and the second sheet-like-member continuous body that have been overlaid on each other in the thickness direction being welded together in the side-seal section; and
the cutting device configured to produce the absorbent article that has the elastic member, the first sheet-like member, and the second sheet-like member,
at a position downstream in the direction of transport with respect to the side-seal-section forming device, the cutting device being performed by cutting the first sheet-like-member continuous body, the elastic-member continuous bodies, and the second sheet-like-member continuous body at each of the cutting target positions.

According to this device for manufacturing an absorbent article, it is possible to achieve actions and effects similar to those in the case of the manufacturing method described above.

Further, an absorbent article comprising:
a first sheet-like member;
a second sheet-like member;
an elastic member that is inserted along a lateral direction between a pair of mutually-opposing facing surfaces of the first sheet-like member;
a plurality of joining portions that for joining together the pair of facing surfaces and that are arranged spacing in the lateral direction,
the joining portions being formed on two sides of the elastic member in a vertical direction so that the elastic member is sandwiched and pressed between the joining portions on the two sides,
the vertical direction being a direction that intersects the lateral direction and a front-rear direction,
the front-rear direction being a direction that intersects the lateral direction; and
a side-seal section that is provided in each lateral end portion,
a portion of at least one of the joining portions being provided at a position laterally outward of the side-seal section in the first sheet-like member in a view of the first sheet-like member in the thickness direction,
the first sheet-like member and the second sheet-like member being overlaid in the front-rear direction and welded in the side-seal section.

According to this absorbent article, a portion of at least one of the joining portions is provided at a position that is laterally outward of the side-seal section in the first sheet-like member. This is a position at which the elastic member is not stretched in the lateral direction when the absorbent article is used. Accordingly, it is possible to suppress detachment that can occur if the elastic member is stretched in the lateral direction, that is to say the vertical contraction of the elastic member due to the foregoing stretching causes relaxation of the pressed state of the elastic member sandwiched between the joining portions. Accordingly, it is possible to suppress the detachment of the lateral end portions of the elastic members from the sheet-shaped member.

Figure 2:
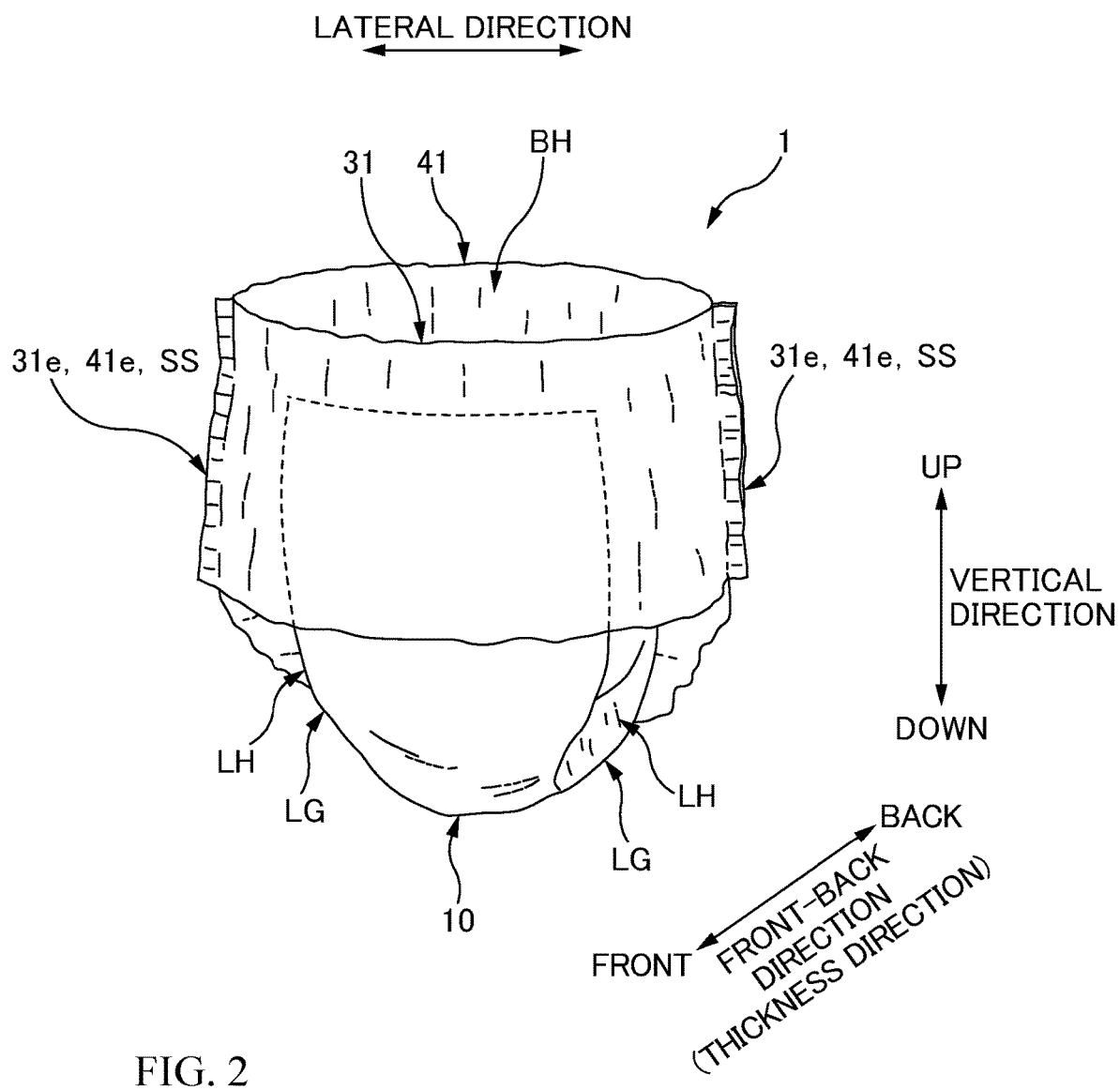
FIG. 2 is a schematic perspective view of a three piece-type of diaper 1 as one example of an absorbent article of one or more embodiments.

A method and a device for manufacturing an absorbent article according to one or more embodiments of the present invention are used in, for example, a manufacturing line for a disposable diaper 1 that is one example of an absorbent article. FIG. 2 is a schematic perspective view of a three piece-type of diaper 1 as one example of the diaper 1 according to one or more embodiments.

In the underpants-shaped state before being worn as shown in FIG. 2, the diaper 1 has a vertical direction, a lateral direction that is orthogonal to the vertical direction, and a "front-back direction" that is orthogonal to the vertical direction and the lateral direction. The vertical direction often conforms to the up-down direction when the diaper 1 is worn. For this reason, hereinafter, the vertical direction will also be called the up-down direction.

Note that with respect to the up-down direction, the upper side corresponds to the waist side of the wearer, and the lower side corresponds to the crotch side of the wearer. Also, with respect to the front-back direction, the front side corresponds to the stomach side of the wearer, and the back side corresponds to the back side of the wearer. Furthermore, with respect to the lateral direction, one side corresponds to the left side of the wearer, and the other side corresponds to the right side of the wearer.

In the underpants-shaped state shown in FIG. 2, the diaper 1 includes: a front band member 31 that extends in the lateral direction; a back band member 41 that extends along the lateral direction, is located on the back side of the front band member 31, and is for forming a waist opening BH on the upper side in the vertical direction along with the front band member 31; and an absorbent main body 10 that is a crotch portion provided between the front band member 31 and the back band member 41. The absorbent main body 10 is arranged at a position protruding farther downward in the vertical direction than the front band member 31 and the back band member 41 do.

Also, lateral end portions 31e of the front band member 31 and corresponding lateral end portions 41e of the back band member 41 are joined in side-seal sections SS. Accordingly, the front band member 31 and the back band member 41 respectively form leg openings LH on two lateral sides on the lower side along with the absorbent main body 10.

Figure 3:
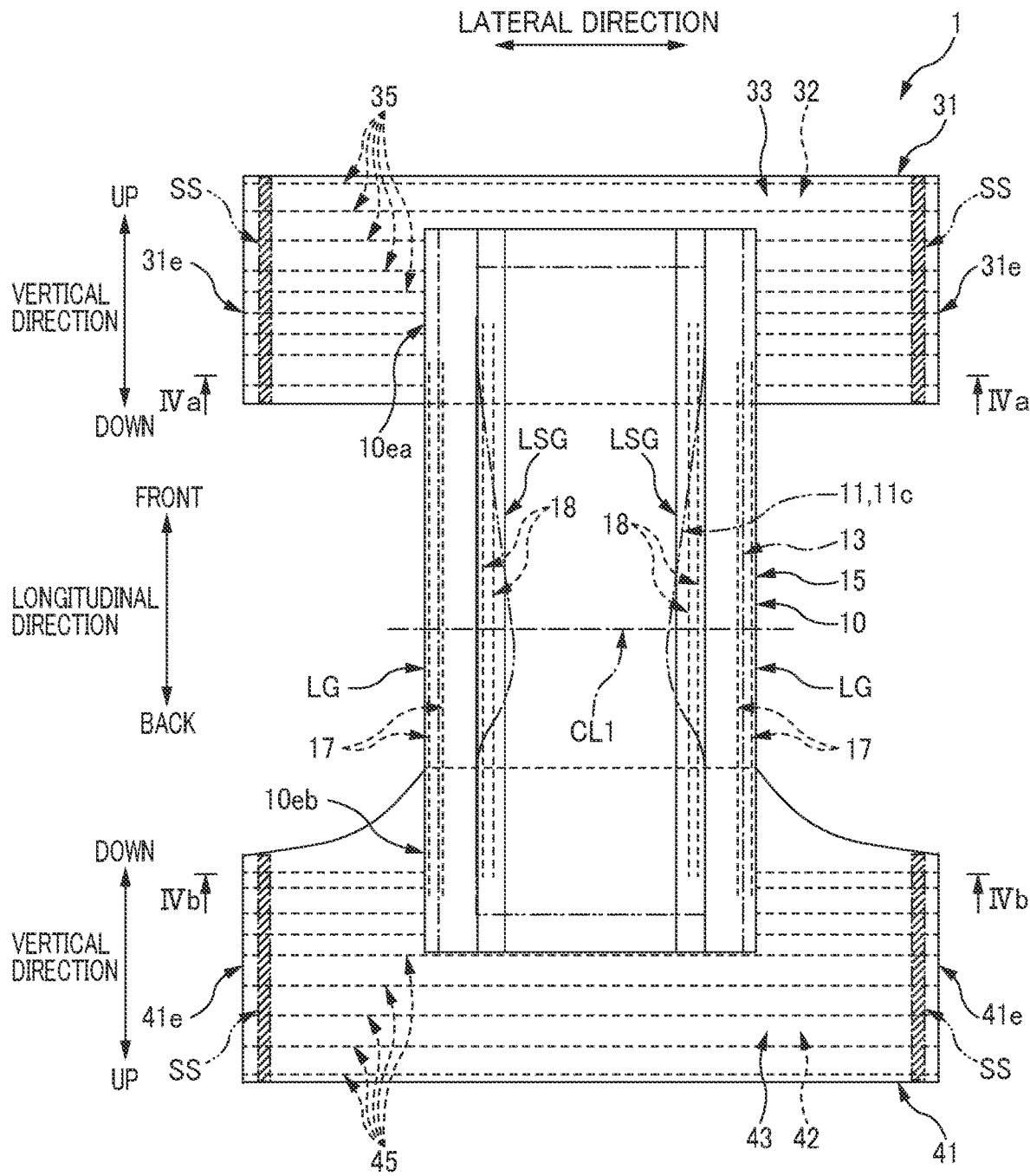
FIG. 3 is a schematic plan view of the diaper 1 in an unfolded state as viewed from a wearer's skin side.

FIG. 3 is a schematic plan view of the diaper 1 in an unfolded state as viewed from the wearer's skin side. Also, FIG. 4 includes a cross-sectional view along IVa-IVa and a cross-sectional view along IVb-IVb in FIG. 3.

Here, the unfolded state is a state in which the aforementioned side-seal sections SS on the two lateral sides of the diaper 1 in the underpants-shaped state shown in FIG. 2 are detached such that the front band member 31 and the back band member 41 separate from each other and the diaper 1 is opened in the vertical direction, and thus the diaper 1 is unfolded in a plan view.

Also, in this unfolded state, the diaper 1 is shown in a virtual state in which there is no stretchability in the members that constitute the diaper 1. For example, although the diaper 1 is provided with elastic members 17, 18, 35, and 45 for the purpose of giving stretchability to the diaper 1 in this example, in the aforementioned unfolded state, the diaper 1 is shown in a virtual state in which the elastic members 17, 18, 35, and 45 have no stretchability (contractive force) whatsoever.

In the unfolded state, the diaper 1 has a longitudinal direction, a lateral direction, and a thickness direction (direction passing through the paper plane in FIG. 3) as three directions that are orthogonal to each other. Note that the longitudinal direction conforms the previously described vertical direction. Also, with respect to the longitudinal direction, one side corresponds to the stomach side, and the other side corresponds to the back side. Also, the outer side in the longitudinal direction corresponds to the upper side in the vertical direction, and the inner side in the longitudinal direction corresponds to the lower side in the vertical direction. Given that the longitudinal direction and the vertical direction are directions that resemble each other in this way, for the sake of convenience hereinafter, the vertical direction will sometimes be used in place of the longitudinal direction in the unfolded state as well. Furthermore, the lateral direction is synonymous with the lateral direction in the previously described underpants-shaped state. Moreover, with respect to the thickness direction, one side corresponds to the skin side that comes into contact with the wearer's body, and the other side corresponds to the opposite non-skin side. Note that the thickness direction conforms to the previously described front-back direction.

In the unfolded state shown in FIG. 3, the front band member 31 is arranged extending in the lateral direction, and the back band member 41 is arranged extending in the lateral direction at a position that is separated from the front band member 31 by a predetermined gap in the longitudinal direction. The absorbent main body 10 spans along the longitudinal direction between the front band member 31 and the back band member 41, and longitudinal end portions 10ea and 10eb of the absorbent main body 10 are respectively joined and fixed to the closest band members 31 and 41, thus forming a substantially H-like outer shape in a plan view. The diaper 1 in this state is folded one time at a folding position that is at a predetermined longitudinal position CL1 of the absorbent main body 10 (a longitudinal central position CL1 of the diaper 1), and the lateral end portions 31e and 41e of the band members 31 and 41, which face each other in the folded state, are joined to each other in the previously described side-seal sections SS. Accordingly, the band members 31 and 41 become connected to each other in a ring shape, thus obtaining the diaper 1 in the underpants-shaped state in which the waist opening BH and the pair of leg openings LH are formed as shown in FIG. 2.

Figure 4:
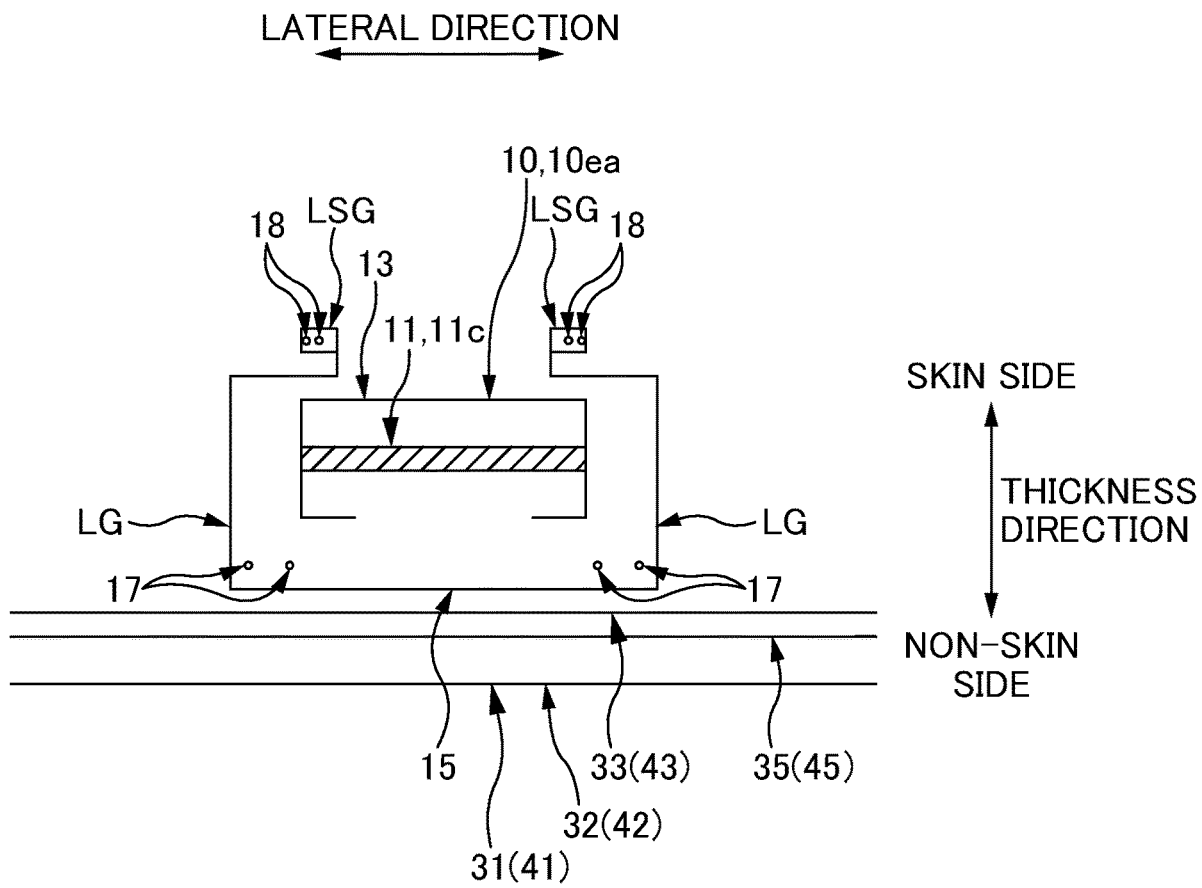
FIG. 4 includes a cross-sectional view along IVa-IVa and a cross-sectional view along IVb-IVb in FIG. 3.

The absorbent main body 10 has an approximately rectangular shape in a plan view in the unfolded state shown in FIG. 3. The longitudinal direction of the absorbent main body 10 conforms to the longitudinal direction of the diaper 1. Also, as shown in FIG. 4, the absorbent main body 10 includes: an absorbent body 11; a liquid-permeable top sheet 13 that covers the absorbent body 11 from the skin side and forms the skin-side surface of the absorbent main body 10; and a liquid-impermeable back sheet 15 that covers the absorbent body 11 from the non-skin side and forms the non-skin side of the absorbent main body 10.

The absorbent body 11 has a liquid-absorbent absorbent core 11c, and a core-wrapping sheet (not shown) that covers the outer circumferential surface of the core 11c. The absorbent core 11c is a molded body that is made of a predetermined liquid absorbent material such as pulp fiber or superabsorbent polymer, and is approximately hourglass-shaped in a plan view, as one example of a predetermined shape. The core-wrapping sheet can be made of a liquid-permeable sheet such as tissue paper or nonwoven fabric, but the core-wrapping sheet is not required to be provided. Also, the absorbent core 11c is not limited in any way to having the aforementioned approximately hourglass-like shape in a plan view, and may have another shape.

The top sheet 13 is a liquid-permeable soft sheet made of nonwoven fabric or the like. The back sheet 15 is also a liquid-impermeable soft sheet. One example of the back sheet 15 is a double-layer structure laminate sheet 15 including: a liquid-impermeable leak-proof sheet made of a polyethylene film (PE) or a polypropylene film; and an exterior sheet that is made of nonwoven fabric and is affixed to the non-skin side of the leak-proof sheet.

As shown in FIG. 3, at least the back sheet 15 is a sheet having a planar size according to which it projects from the absorbent body 11 in the longitudinal direction and the lateral direction. Leg gathers LG that stretch and contract in the longitudinal direction are formed in the portions that protrude in the lateral direction. Specifically, elastic strings 17 that serve as elastic members and extend in the longitudinal direction are fixed in the protruding portions in a state of being stretched in the longitudinal direction, thus forming the stretchable leg gathers LG in these portions.

Also, as shown in FIGS. 3 and 4, the absorbent main body 10 has barrier cuffs LSG as leak-proof wall portions in the lateral end portions for the purpose of preventing lateral leakage. Specifically, in the lateral end portions of the absorbent main body 10, a configurations are provided in which elastic strings 18 serving as elastic members 18 and extending in the longitudinal direction are attached, in a state of being stretched in the longitudinal direction, to sheet-like portions that will form the barrier cuffs LSG.

As shown in FIG. 3, the front band member 31 is a sheet-like member that is approximately rectangular in a plan view and is constituted by two nonwoven fabric sheets 32 and 33. Specifically, as shown in FIG. 4, the two nonwoven fabric sheets 32 and 33 are overlaid on each other in the thickness direction. And, the pair of facing surfaces that face each other are joined to each other by welded portions j (corresponding to joining portions) that are arranged discretely spacing in the vertical direction (longitudinal direction) and the lateral direction as shown in later-described FIG. 5. As shown in FIG. 3, the front band member 31 is arranged so as to protrude out from the absorbent main body 10 on the two lateral sides, and is overlaid on and joined to the non-skin side of the front end portion 10ea of the absorbent main body 10.

Also, in this example, spunbond nonwoven fabric is used for both of the two nonwoven fabric sheets 32 and 33 pertaining to the front band member 31. Note that there is no limitation whatsoever to this, and it is possible to use various other types of nonwoven fabric such as SMS (spunbond/meltblown/spunbond) nonwoven fabric. Also, in this example, standalone fibers made of polypropylene (PP), which is a representative example of a thermoplastic, may be used as the constituent fibers of the nonwoven fabric, but there is no limitation whatsoever to this. For example, standalone fibers made of another thermoplastic resin such as polyethylene (PE) may be used, and composite fibers that have a sheath/core structure and are made of PE and PP or the like may be used. Note that the same also applies to the back band member 41 that will be described hereinafter.

Similarly to the front band member 31, the back band member 41 is also a sheet-like member that is approximately rectangular in a plan view and is constituted by two nonwoven fabric sheets 42 and 43. Specifically, as shown in FIG. 4, the two nonwoven fabric sheets 42 and 43 are overlaid on each other in the thickness direction, and, similarly to the front band member 31 shown in FIG. 5, the pair of facing surfaces that face each other are joined to each other by welded portions j (corresponding to second joining portions) that are arranged discretely spacing in the vertical direction (longitudinal direction) and the lateral direction. As shown in FIG. 3, the back band member 41 is arranged so as to protrude out from the absorbent main body 10 on the two lateral sides, and is overlaid on and joined to the non-skin side of the back end portion 10eb of the absorbent main body 10.

Note that when the content described below is the same for both the front band member 31 and the back band member 41, only the front band member 31 will be described as a representative for both, and corresponding portions and the like of the back band member 41 are simply indicated in parentheses.

Figure 5:
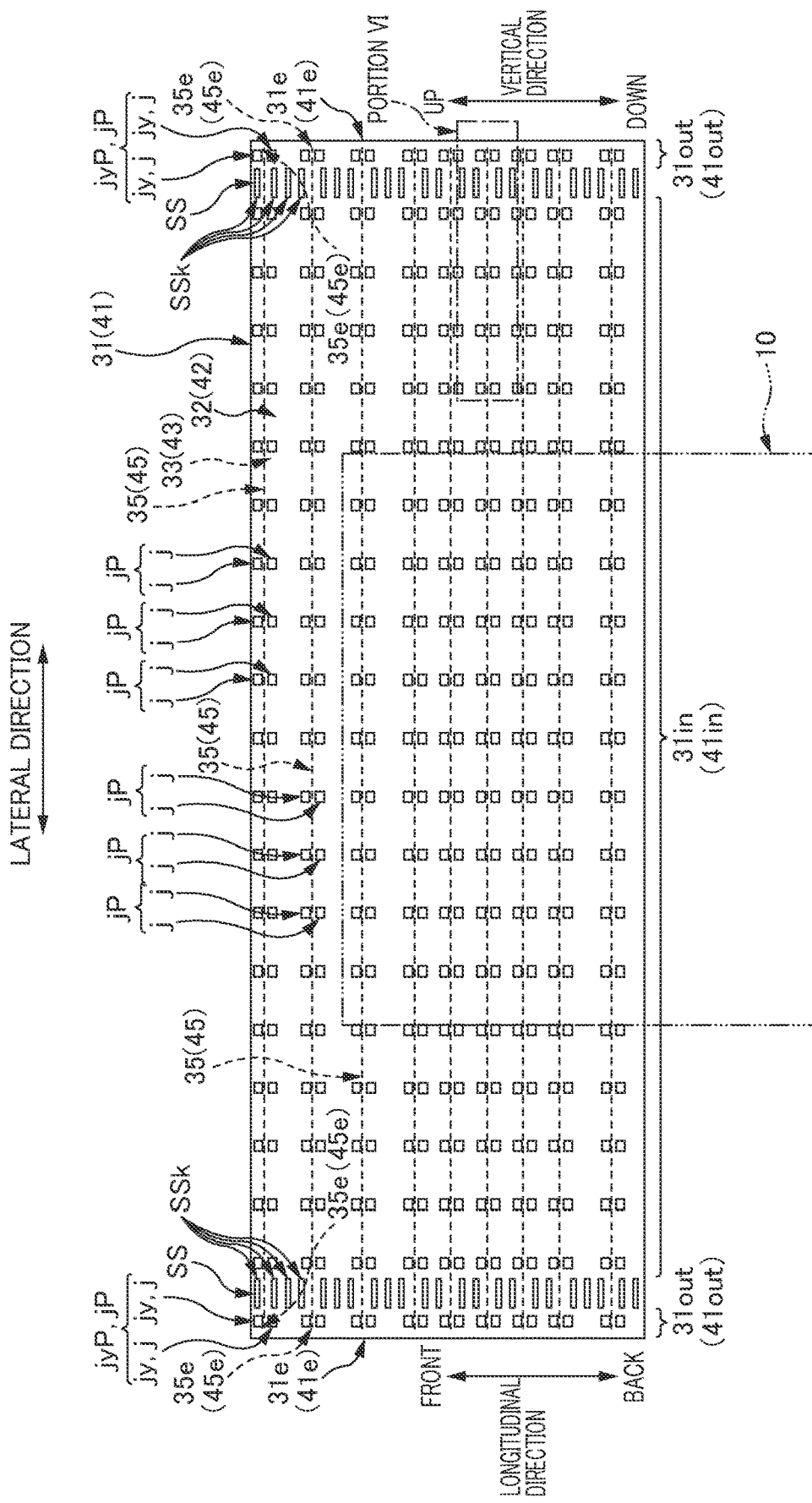
FIG. 5 is a schematic plan view of a front band member 31 in the unfolded state as viewed from the non-skin side.

FIG. 5 is a schematic plan view of the front band member 31 in the unfolded state as viewed from the non-skin side.

As shown in FIG. 5, the previously-described side-seal section SS is provided in each of the two end portions 31e (41e) in the lateral direction of the front band member 31 (41). In this example, the side-seal sections SS have welded portions SSk, SSk . . . that are the same shape as each other and are arranged side-by-side along a straight line that extends in the vertical direction. In the welded portions SSk, the nonwoven fabric sheet 33 of the front band member 31 and the nonwoven fabric sheet 43 of the back band member 41 are welded to each other, and a pair of mutually-opposing facing surfaces of the two nonwoven fabric sheets 32 and 33 pertaining to the front band member 31 are welded to each other, and furthermore, a pair of mutually-opposing facing surfaces of the two nonwoven fabric sheets 42 and 43 pertaining to the back band member 41 are welded to each other.

As shown in FIG. 5, a plurality of elastic strings 35, 35 . . . (45, 45 . . . ), which are elastic members (second elastic members) that extend in the lateral direction, are inserted side-by-side spacing in the vertical direction between the pair of opposing facing surfaces of the two nonwoven fabric sheets 32 and 33 (42 and 43) of the front band member 31 (41).

And the elastic strings 35, 35 . . . (45, 45 . . . ) are attached to the nonwoven fabric sheets 32 and 33 (42 and 43) with use of the welded portions j, j . . . that were mentioned above. Accordingly, the front band member 31 (41) is given stretchability in the lateral direction. Also, the previously mentioned welded portions j, j . . . not only have a function of joining the pair of facing surfaces of the two nonwoven fabrics 32 and 33 (42 and 43) to each other, but also have a function of attaching the elastic strings 35 (45) to the two nonwoven fabric sheets 32 and 33 (42 and 43).

Figure 6A:
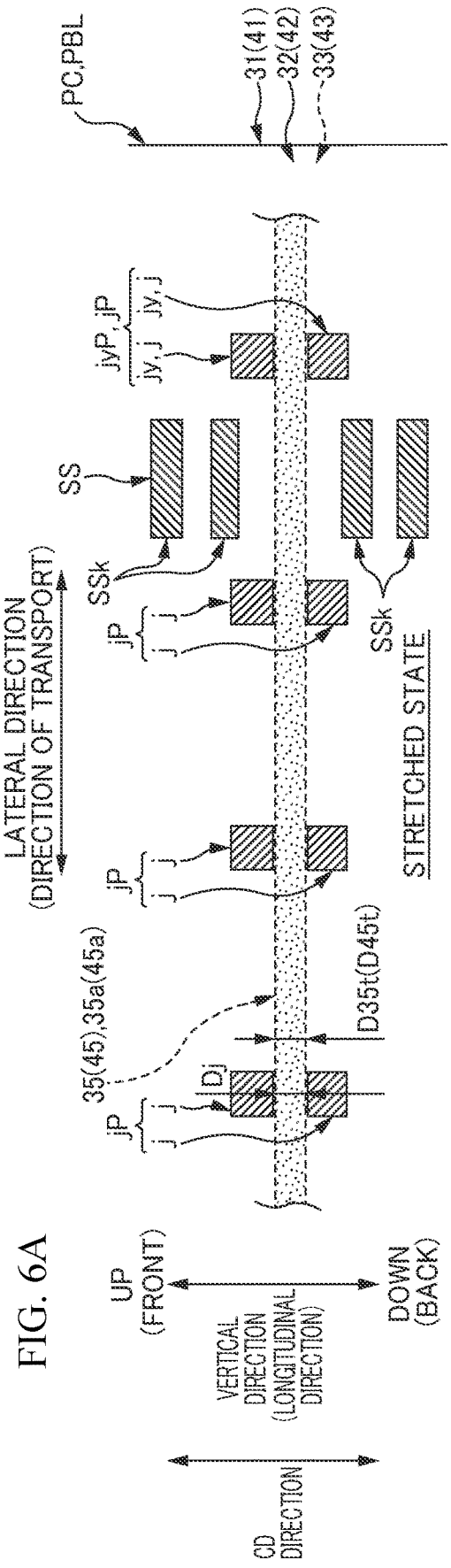
FIGS. 6A and 6B are illustrative views of an elastic string 35 (45) attachment function exhibited by welded portions j.
Figure 6B:
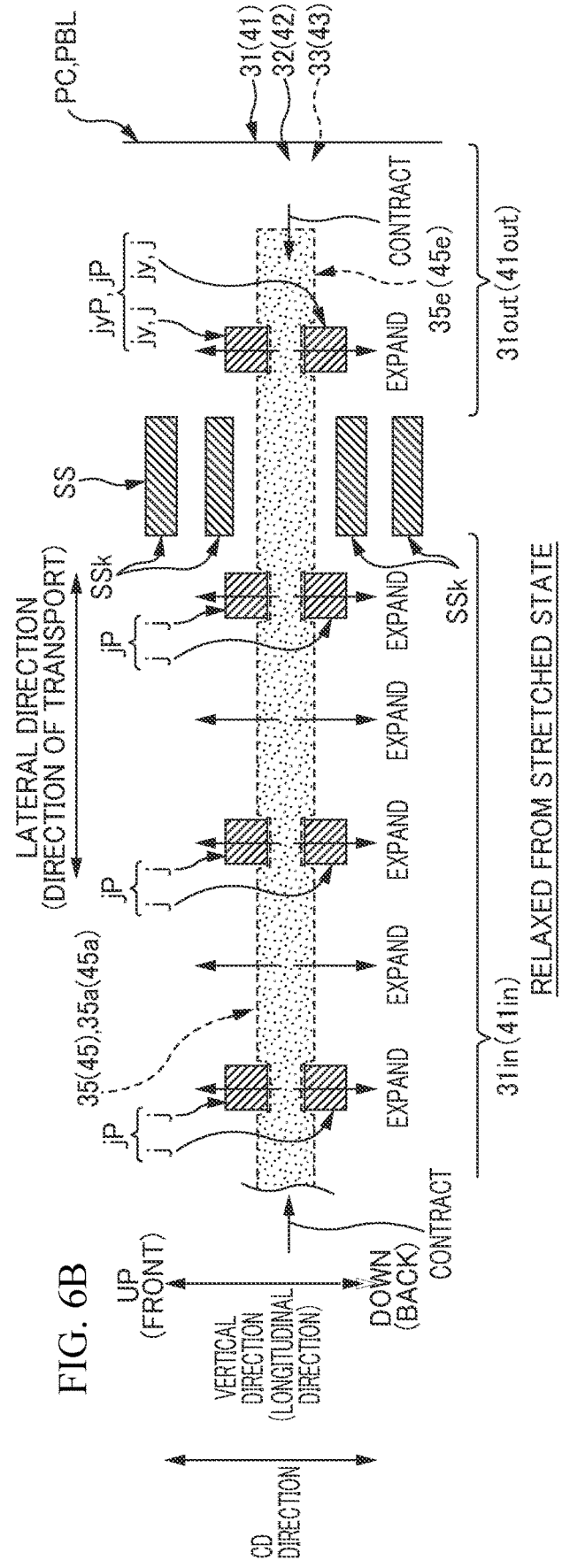

FIGS. 6A and 6B are schematic enlarged views of a portion VI in FIG. 5, and are for illustrating the latter function of the welded portions j, that is to say the function of attaching the elastic strings 35 (45).

As shown in FIG. 5, the welded portions j, j . . . are provided for each of the elastic strings 35 (45) that extend in the lateral direction. Also, the welded portions j are formed in pairs of portions on respective sides of the corresponding elastic string 35 in the vertical direction, that is to say, each pair of welded portions j that are side-by-side in the vertical direction make up welded portion pair jP. These welded portion pairs jP are formed side-by-side in the lateral direction spacing between welded portion pairs jP that are adjacent in the lateral direction. Also, as shown in FIG. 6A, the pair of welded portions j that form each welded portion pair jP are separated by a gap Dj in the vertical direction, and the size of this gap Dj is set the same as or somewhat larger than a vertical size D35t (D45t) of the elastic strings 35 (45) in a state of being stretched to a target stretch factor in the lateral direction. In the diaper 1 in the underpants-shaped state shown in FIG. 2, the elastic strings 35 (45) are relaxed from the state of being stretched to the aforementioned stretch factor. Accordingly, in this underpants-shaped state, as shown in FIG. 6B, the elastic strings 35 (45) contract in the lateral direction and expand in the vertical direction, and here, based on the size relationship described above, the expansion of the elastic strings 35 (45) in the vertical direction is restricted by the pairs of welded portions j. Accordingly, the elastic strings 35 (45) are substantially sandwiched and pressed in the vertical direction by the pairs of welded portions j, and as a result, the elastic strings 35 (45) are attached in the front band member 31 (41).

It should be noted that the aforementioned stretch factor is a value R (=L1/L0) that indicates the ratio of a stretched total length L1 of the elastic string 35 (45) to a total length L0 in a natural no-load state. The aforementioned target stretch factor is selected from the range of 1.5 to 4.0, for example.

Also, as shown in FIGS. 5 and 6B, when viewing the front band member 31 (41) in the thickness direction, a portion of at least one of the welded portions j is provided in an outward portion 31out that is outward of the side-seal section SS in the lateral direction. Hereinafter, the outward portion 31out will also be called the "margin portion 31out", a welded portion jy that is at least partially provided in the margin portion 31out will also be called a "margin welded portion jy", and as long as the margin welded portion jy is provided, it is possible to suppress the following.

First, as shown in FIG. 5, the front band member 31 (41) includes a portion 31in (41in) that exists laterally inward of the welded portions SSk of the side-seal sections SS, and this portion is a portion that comes into contact with the stomach side of the wearer's torso. For this reason, the inward portion 31in (41in) is given stretchability in the lateral direction by the elastic strings 35 (45).

When the diaper 1 is used, the inward portion 31in (41in) stretches in the lateral direction, and the elastic strings 35 (45) also stretch in the lateral direction at that time. Accordingly, due to this stretching, the elastic strings 35 (45) contract in the vertical direction that intersects the lateral direction, and as a result, the state in which the elastic strings 35 (45) are sandwiched and pressed between pairs of the welded portions j is relaxed. If this relaxation occurs in lateral end portions 35e (45e) of the elastic strings 35 (45), there is a risk that the lateral end portions 35e (45e) will detach from the pairs of joining portions j at the lateral ends first, and then successively from the pairs of welded portions j inward thereof, and that, as a result, the elastic strings 35 (45) will detach from the pairs of welded portions j over a wide range in the inward portion 31in (41in) as previously described with reference to the partial enlarged views in FIG. 1A.

In view of this, the previously described margin portions 31out (41out), which are the portions 31out (41out) that are laterally outward of the side-seal sections SS in the front band member 31 (41) in FIGS. 5, 6A, and 6B, are portions that are not stretched in the lateral direction when the diaper 1 is used. For this reason, if the previously described pairs of margin welded portions jy are provided in the margin portions 31out (41out), even when the diaper 1 is used, there is no relaxation of the pressed state of the elastic strings 35 (45) sandwiched between the pairs of margin welded portions jy, and the securely pressed state of the elastic strings 35 (45) can be maintained. This makes it possible to prevent the detachment of the end portions 35e (45e) of the elastic strings 35 (45) from the pairs of welded portions j (including the margin welded portions jy) of the front band member 31 (41).

Also, in this example in FIG. 5, the margin welded portions jy are entirely provided in the margin portion 31out (41out). Accordingly, the above-described pressed state can be maintained more reliably.

Note that although the margin welded portion jy is provided for all of the elastic strings 35, 35 . . . (45, 45 . . . ) that are provided in the front band member 31 (41) in the example in FIG. 5, there is no limitation whatsoever to this. For example, concerning all of the elastic strings 35 (45) pertaining to the front band member 31 (41), as long as the margin welded portion jy is provided for at least one of the elastic strings, one-third or more of the elastic strings, half or more of the elastic strings, or two-thirds or more of the elastic strings, it is possible to suppress the stretching of the elastic strings 35 (45) that are provided with the margin welded portion jy. For this reason, elastic strings 35 (45) not provided with the margin welded portion jy may exist among the elastic strings 35 (45) pertaining to the front band member 31 (41).

Figure 7:
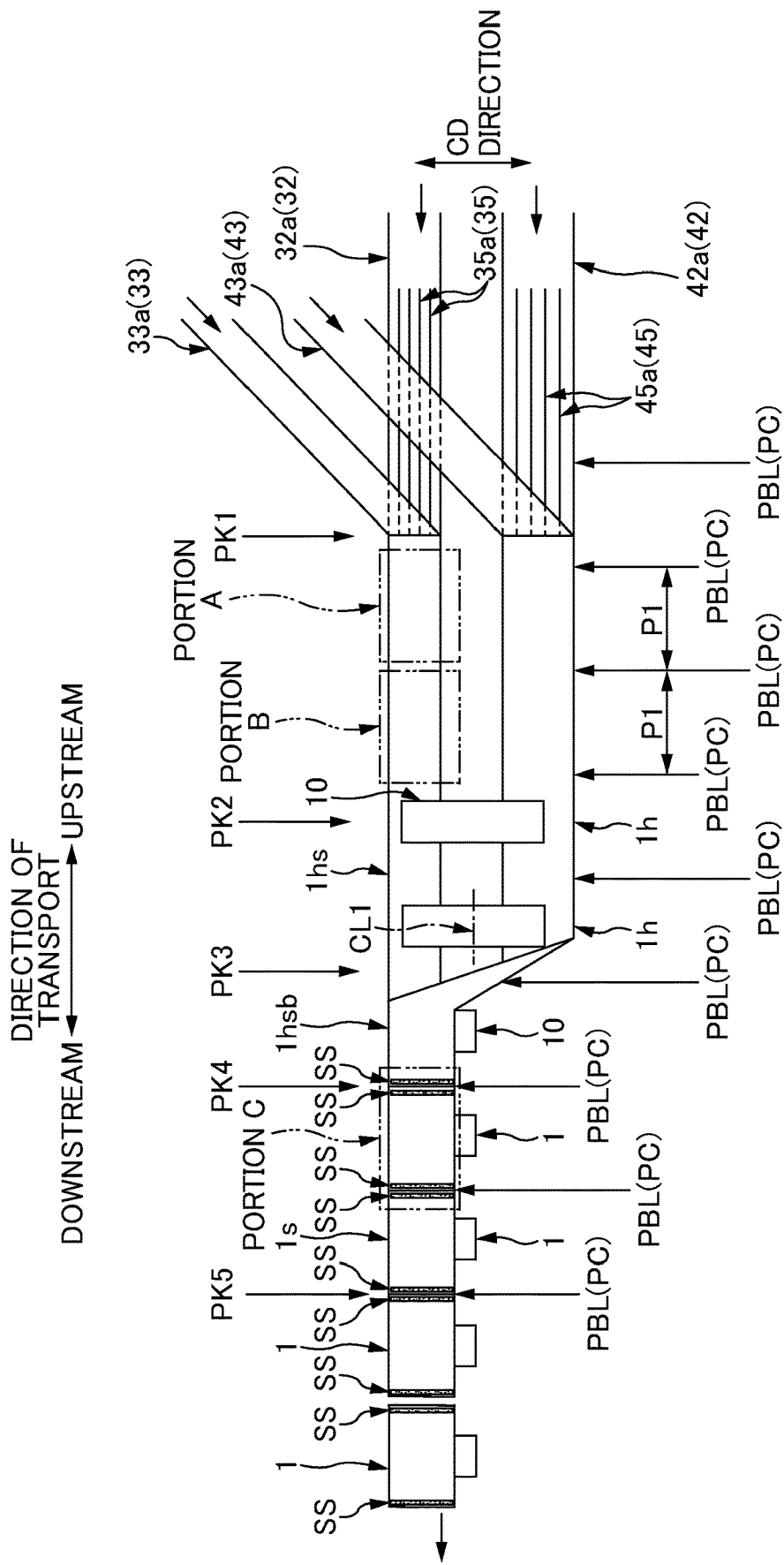
FIG. 7 is a schematic plan view showing a partial perspective view of how the diaper 1 is manufactured in a manufacturing line.
Figure 8A:
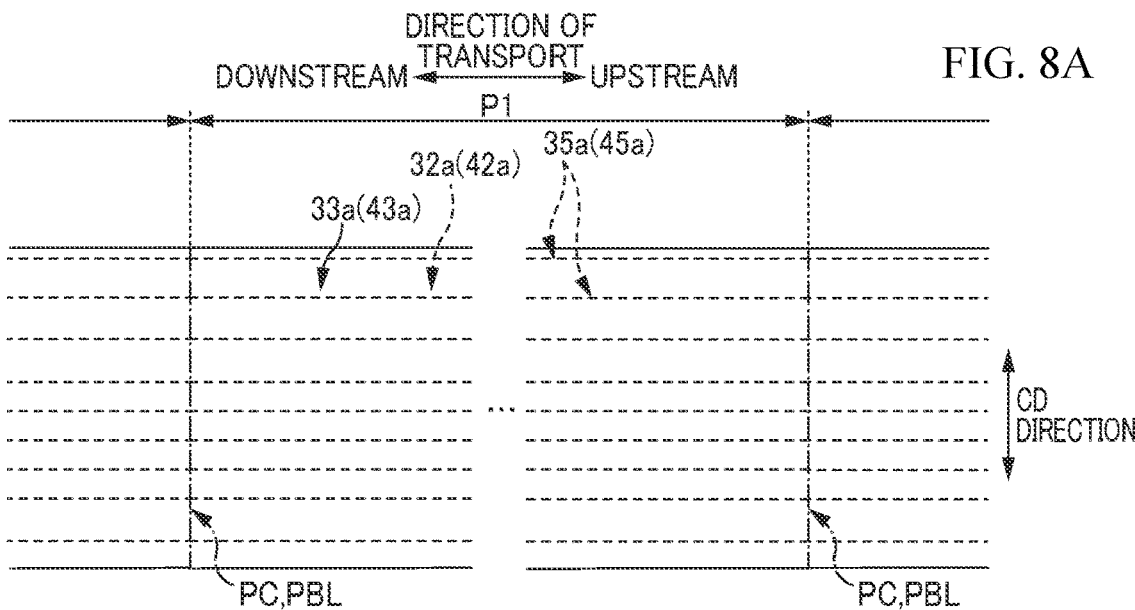
FIGS. 8A, 8B, and 8C are respectively schematic enlarged views of portions A, B, and C in FIG. 7.
Figure 8B:
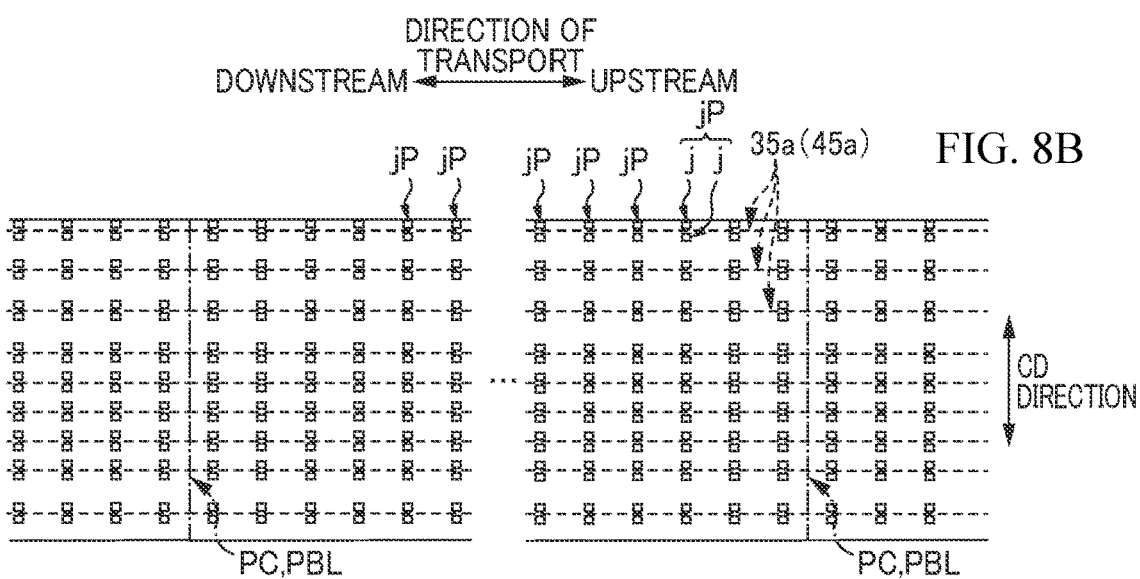
Figure 8C:
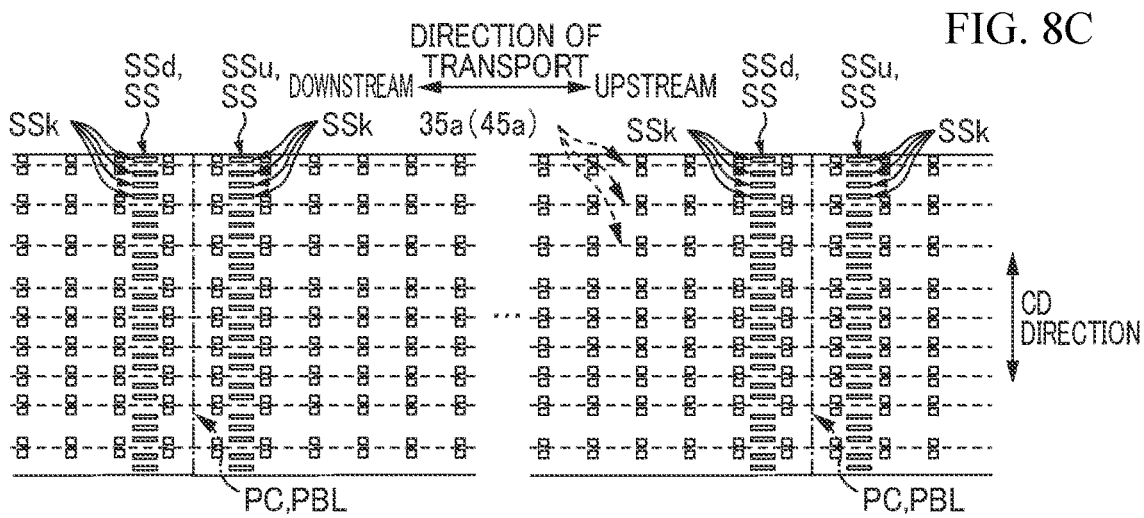

This diaper 1 is manufactured in a manufacturing line. FIG. 7 is a schematic plan view showing a partial perspective view of the manufacturing of the diaper 1 in the manufacturing line. Also, FIGS. 8A, 8B, and 8C are respectively schematic enlarged views of portions A, B, and C in FIG. 7. It should be noted that, more specifically, in FIG. 8C, the continuous sheets 42a and 43a pertaining to the back band member 41 would originally be visible instead of the continuous sheets 32a and 33a pertaining to the front band member 31, but for the sake of convenience in the description, it is assumed that the continuous sheets 32a and 33a pertaining to the front band member 31 are visible in the following description. Note that the same applies to later-described FIGS. 9 to 12 as well.

In this manufacturing line, for example, the two nonwoven fabric sheets 32 and 33 (corresponding to first sheet-like members) pertaining to the front band member 31 are transported in the form of continuous sheets 32a and 33a (corresponding to a first sheet-like-member continuous body) that are continuous in the direction of transport, and likewise, the two nonwoven fabric sheets 42 and 43 (corresponding to second sheet-like members) pertaining to the back band member 41 are transported in the form of continuous sheets 42a and 43a (corresponding to a second sheet-like-member continuous body) that are continuous in the direction of transport. The continuous sheets 32a, 33a, 42a, and 43a pass through processing positions PK1 to PK5 that are set in the direction of transport, and the continuous sheets 32a, 33a, 42a, and 43a are subjected to processing processes that correspond to the processing positions PK1, PK2, and so on.

Note that here, the direction that is orthogonal to both the thickness direction and the direction of transport of the continuous sheets 32a, 33a, 42a, and 43a is defined as "CD direction", and in this example, the continuous sheets 32a, 33a, 42a, and 43a (i.e., the two continuous sheets 32a and 33a pertaining to the front band member 31 and the two continuous sheets 42a and 43a pertaining to the back band member 41) are transported side-by-side in the CD direction. Note that there is no limitation whatsoever to this.

Also, in this example, the above-described processing positions, namely the first to fifth processing positions PK1 to PK5, are set side-by-side in this order from upstream to downstream in the direction of transport. At the processing positions PK1, PK2, and so on, the processes that are performed on the continuous sheets 32a and 33a pertaining to the front band member 31 are substantially the same as those performed on the two continuous sheets 42a and 43a pertaining to the back band member 41. For this reason, the front band member 31 and the back band member 41 will not be distinguished from each other when the same content applies hereinafter. For example, in the following description, the term "band member 31 (41)" will simply be used, or the term "the two continuous sheets 32a and 33a (42a and 43a)" will simply be used. Note that in such cases, in the terms indicating the members, such as "the continuous sheets 32a and 33a (42a and 43a)", "the elastic strings 35 (45)", and "the elastic-string continuous bodies 35a (45a)", the reference signs that immediately follow the terms are the reference signs pertaining to the front band member 31, and the subsequent reference signs in the parentheses are the reference signs pertaining to the back band member 41.

As shown in FIG. 7, the two continuous sheets 32*a* and 33*a* (42*a* and 43*a*) pertaining to the band member 31 (41) are transported in a so-called lateral flow. Specifically, the two continuous sheets 32*a* and 33*a* (42*a* and 43*a*) are transported such that the direction corresponding to the lateral direction of the diaper 1 conforms to the direction of transport.

For this reason, in the two continuous sheets 32*a* and 33*a* (42*a* and 43*a*), boundary positions PBL between two diapers 1 that are adjacent in the lateral direction are virtually set at a product pitch P1 in the direction of transport. Also, at the fifth processing position PK5 located at the end of the manufacturing line, the boundary position PBL is a cutting target position PC at which the two continuous sheets 32*a* and 33*a* (42*a* and 43*a*) are cut to produce a single-cut diaper 1.

Note that the two continuous sheets 32*a* and 33*a* (42*a* and 43*a*) pertaining to the band member 31 (41) are transported by appropriate transporting devices (not shown) such as a belt conveyor and transporting rollers. Accordingly, unless particularly stated otherwise, it is assumed that the two continuous sheets 32*a* and 33*a* (42*a* and 43*a*) are transported in the direction of transport by such transporting devices. Examples of the belt conveyor includes a normal belt conveyor that has an endless belt that is driven to rotate as a transporting surface, and a suction belt conveyor that has a function for suction to the outer circumferential surface of an endless belt.

Also, in this example, the stretchability of the continuous sheets 32*a*, 33*a*, 42*a*, and 43*a* is much smaller than the stretchability of the elastic strings 35 and 45, to the extent that such stretchability can be ignored. The continuous sheets 32*a*, 33*a*, 42*a*, and 43*a* are then transported from the first processing position PK1 to the fifth processing position PK5 while being stretched in the direction of transport.

The following is a detailed description of the diaper 1 manufacturing process.

As shown in FIG. 7, first, the two continuous sheets 32*a* and 33*a* (42*a* and 43*a*) pertaining to the band member 31 (41) pass the first processing position PK1. While passing, as shown in FIGS. 7 and 8A, the two continuous sheets 32*a* and 33*a* (42*a* and 43*a*) are overlaid on each other in the thickness direction. At this time, the elastic-string continuous bodies 35*a*, 35*a* . . . (45*a*, 45*a* . . . ), which are elastic-member continuous bodies (second elastic-member continuous bodies) and are continuous in the direction of transport, are inserted and arranged side-by-side spacing in the CD direction between the two mutually-opposing facing surfaces of the two continuous sheets 32*a* and 33*a* (42*a* and 43*a*), in a state of being stretched to the previously described target stretch factor in the direction of transport (corresponding to an arranging step and a second arranging step).

Note that the elastic-string continuous bodies 35*a* (45*a*) are arranged on the pair of facing surfaces by a transporting device (corresponding to an arranging device) such as transporting rollers (not shown).

Also, at the same time as this overlaying or immediately thereafter, as shown in FIG. 8B, the previously described welded portions j, j . . . are formed as joining portions (second joining portions) in the two continuous sheets 32*a* and 33*a* (42*a* and 43*a*), and thus the pair of facing surfaces of the two continuous sheets 32*a* and 33*a* (42*a* and 43*a*) are joined to each other by the welded portions j, j . . . (corresponding to a joining-portion forming step and a second joining-portion forming step).

Here, as previously described, in this manufacturing line, the lateral direction of the diaper 1 conforms to the direction of transport, and the vertical direction of the diaper 1 conforms to the CD direction. For this reason, the welded portions j are formed in pairs, on two sides in the CD direction of the elastic-string continuous bodies 35*a* (45*a*). Specifically, as shown in FIG. 8B, two welded portions j that are side-by-side on respective sides in the CD direction of each continuous body 35*a* (45*a*) form a welded portion pair jP. These welded portion pairs jP are formed side-by-side in the direction of transport spacing between welded portion pairs jP that are adjacent in the direction of transport.

Also, as shown in FIG. 6A, the two welded portions j that form each welded portion pair jP are separated by the gap Dj in the CD direction, and here, the size of the gap Dj is the same as or somewhat larger than the size D35*t* (D45*t*) in the CD direction of the elastic-string continuous bodies 35*a* (45*a*) which are located at the first processing position PK1 and which are in a state of being stretched to the target stretch factor in the direction of transport.

Accordingly, when the elastic-string continuous bodies 35*a* (45*a*) are cut at the later-described fifth processing position PK5 thus relaxing the stretched state of the elastic strings 35 (45), as shown in FIG. 6B, the elastic strings 35 (45) contract in the direction of transport and attempt to expand in the CD direction. But, the elastic strings 35 (45) are sandwiched and pressed in the CD direction between the pair of welded portions j, and thus the elastic strings 35 (45) are attached to the two nonwoven fabric sheets 32 and 33 (42 and 43) of the band member 31 (41).

Figure 9:
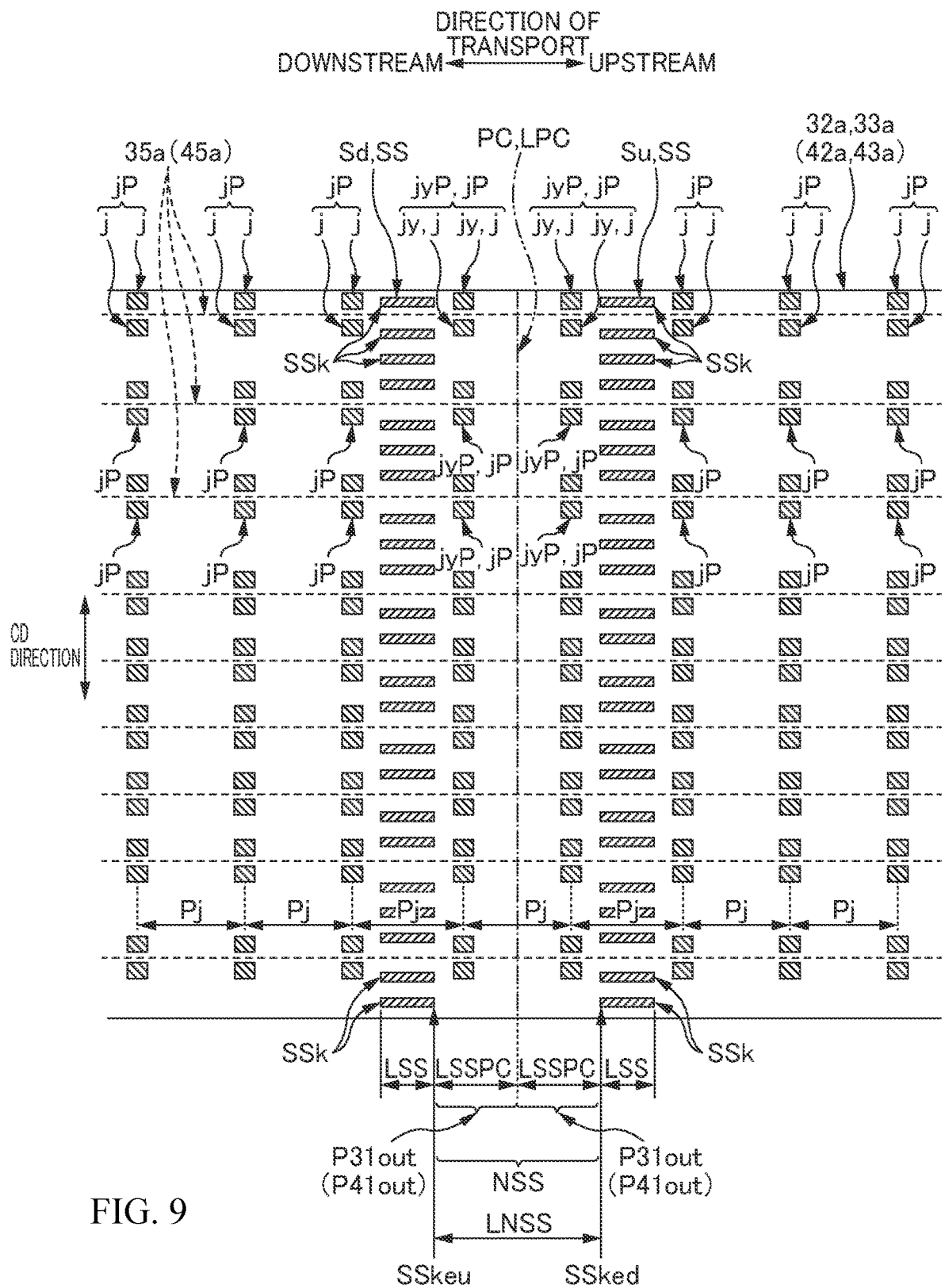
FIG. 9 is an enlarged view of a portion in FIG. 8C.

Note that as shown in FIG. 9 which is the enlarged view of a portion of FIG. 8C, when viewing the continuous sheets 32*a* and 33*a* (42*a* and 43*a*) in the thickness direction, a portion of at least one welded portion jy is located between the cutting target position PC and the side-seal section SS that is to be subsequently formed. In other words, the margin welded portion jy is provided at a position P31out (P41out) that corresponds to the previously described margin portion 31out (41out). Accordingly, when cutting of the elastic-string continuous bodies 35*a*, 35*a* . . . (45*a*, 45*a* . . . ) at the cutting target position PC along with the two continuous sheets 32*a* and 33*a* (42*a* and 43*a*) is performed at the later-described fifth processing position PK5, the end portions 35*e* (45*e*) of the relaxed elastic strings 35 (45) can be sandwiched and pressed between pairs of the margin welded portions jy. Accordingly, as shown in FIG. 5, the end portions 35*e* (45*e*) are stopped at the position of the margin portion 31out (41out) where stretching does not occur in the lateral direction during usage of the diaper 1. Accordingly, the end portions 35*e* (45*e*) can also be prevented from stretching during usage of the diaper 1, and as a result, it is possible to suppress the case where the end portions 35*e* (45*e*) detach from the pairs of margin welded portions jy in the band members 31 (41) during usage of the diaper 1.

Also, in this example in FIG. 9, the margin welded portions jy are entirely provided between the side-seal section SS and the cutting target position PC. Accordingly, the above-described being sandwiched and pressed can be achieved reliably, thus making it possible to reliably suppress the case where the end portions 35*e* (45*e*) of the elastic strings 35 (45) detach from the pairs of margin welded portions jy.

Note that the margin welded portions jy are reliably provided by performing the following, for example. First, as shown in FIG. 9, several welded portions j, j . . . are provided at a predetermined formation pitch Pj in the direction of transport so as to span and extend beyond the cutting target position PC and the positions of the two side-seal sections SS located on the two direction-of-transport sides of the cutting target position PC. In this example, the welded portions j, j . . . are provided at the formation pitch Pj over the entire length in the direction of transport. Also, letting portions NSS of the continuous sheets 32a and 33a (42a and 43a) that are located between the two side-seal sections SS and do not have the side-seal sections SS formed therein be called side-seal-portion-non-formation portions NSS, the following relation of size at the fourth processing position PK4 is set: the formation pitch Pj is smaller than half of a direction-of-transport size LNSS (=LNSS/2) of the side-seal-portion-non-formation portions NSS. According to this configuration, a portion of at least one welded portion j can be reliably formed at the position P31out (P41out) that is between the side-seal section SS and the cutting target position PC in the direction of transport, that is to say the position P31out (P41out) that corresponds to the margin portion 31out (41out) in the continuous sheets 32a and 33a (42a and 43a). In other words, the above-described margin welded portions jy can be formed reliably.

Note that the direction-of-transport size LNSS of the side-seal-portion-non-formation portion NSS can be defined as follows. First, in this example, as shown in FIG. 9, the side-seal sections SS on the two sides of the cutting target position PC are each constituted by a plurality of welded portions SSk, SSk . . . ; the welded portions SSk, SSk . . . have the same shape and are side-by-side along one straight line that extends in the CD direction. Here, the two side-seal sections SS respectively downstream and upstream in the direction of transport with respect to the cutting target position PC are called a downstream side-seal section SSd and an upstream side-seal section SSu respectively. In this case, the size of the direction-of-transport space between a direction-of-transport upstream end SSkeu of the welded portion SSk in the downstream side-seal section SSd and a direction-of-transport downstream end SSked of the welded portion SSk in the upstream side-seal section SSu is the direction-of-transport size LNSS of the side-seal-portion-non-formation portion NSS.

Also, the direction-of-transport size LSS of the side-seal section SS in FIG. 9 and the direction-of-transport size LSSPC of a space between the side-seal section SS and the cutting target position PC will be mentioned later in the description, and these sizes are defined as follows. The size LSS is a direction-of-transport size LSSk of the welded portion SSk, and the size LSSPC is the size of the direction-of-transport space between the cutting target position PC and the upstream end SSkeu of the welded portion SSk in the downstream side-seal section SSd for example.

However, although not shown, if the side-seal section SSd and SSu have a plurality of welded portions SSk, SSk . . . in the direction of transport, the above-described definition cannot apply, and the sizes are defined as follows. Specifically, in this case, the upstream end SSkeu of the welded portion SSk that is located the most upstream in the direction of transport in the downstream side-seal section SSd is the upstream end SSdeu of the downstream side-seal section SSd. Similarly, the downstream end SSked of the welded portion SSk that is located the most downstream in the direction of transport in the upstream side-seal section SSu is the downstream end SSued of the upstream side-seal section SSu. Accordingly, the size LNSS of the side-seal-portion-non-formation portion NSS is the size of the direction-of-transport space between the upstream end SSkeu of the most upstream welded portion SSk of the downstream side-seal section SSd and the downstream end SSked of the most downstream welded portion SSk of the upstream side-seal section SSu.

Also, the above-described direction-of-transport size LSS of the side-seal section SS is the size of the direction-of-transport space between the upstream end SSkeu of the most upstream welded portion SSk and the downstream end SSked of the most downstream welded portion SSk in the side-seal section SS. Also, the direction-of-transport size LSSPC of the space between the side-seal section SS and the cutting target position PC is the size of the space between the upstream end SSkeu of the most upstream welded portion SSk in the side-seal section SS and the cutting target position PC located upstream with respect to the side-seal section SS.

In this example in FIG. 9, a plurality of the elastic-string continuous bodies 35a (45a) are provided side-by-side in the CD direction, and a welded portion pair jP is provided for each of the elastic-string continuous bodies 35a (45a). These welded portion pairs jP, jP . . . are provided in a lattice-like arrangement over the entire surface of the continuous sheets 32a and 33a (42a and 43a) of the band member 31 (31). In other words, the pairs are provided at intersections between virtual lines that extend in the direction of transport and virtual lines that extend in the CD direction. Lastly, in the state of the diaper 1 in FIG. 2, at lateral (direction-of-transport) positions in the vicinity of the welded portion pairs jP, due to lateral contraction of the elastic strings 35, wrinkles form in the nonwoven fabric sheets 32 and 33 (42 and 43) pertaining the band members 31 (41) in FIG. 5. In view of this, in this example in FIG. 9, as previously described, all of the welded portion pairs jP, jP . . . , which are side-by-side in the CD direction (vertical direction) are aligned on a virtual line that extends in the CD direction. For this reason, the wrinkles are also aligned in a similar manner. Accordingly, these wrinkles can be presented in an orderly arrangement, and this makes it possible to improve the appearance of the band members 31 (41) of the diaper 1 in FIG. 2.

Also, this orderly arrangement of the wrinkles similarly applies at the position P31out (P41out) corresponding to the margin portion 31out (41out). In other words, at the position P31out (P41out) corresponding to the margin portion 31out (41out), the margin welded portion pairs jyP each made up of two margin welded portions jy that are side-by-side in the CD direction are provided for each of the elastic-string continuous bodies 35a (45a). In addition, all of the margin welded portion pairs jyP, jyP . . . , which are side-by-side in the CD direction, are located on a virtual line that extends in the CD direction. Accordingly, in the state of the diaper 1 in FIG. 2, in the margin portion 31out (41out) in FIG. 5 as well, the wrinkles can be presented in an orderly arrangement, and it is therefore possible to improve the appearance of the margin portion 31out (41out).

Note that there is no limitation whatsoever to this. Specifically, as long as at least three welded portion pairs jP among all of the welded portion pairs jP, jP . . . that are side-by-side in at least the CD direction (vertical direction) are located on the virtual line that extends in the CD direction, it is possible to suitably achieve the above-described effect of improving the appearance. For this reason, there is no need for all of the welded portion pairs jP, jP . . . that are side-by-side in the CD direction to be in the above-described positional relationship. For example, a configuration is possible in which one-third or more, half or more, or two-thirds or more of the welded portion pairs jP, jP . . . are in the above-described positional relationship. Also, the virtual line on which the at least three welded portion pairs jP are to be located is not required in any way to extend in the CD direction. The virtual line needs only extend in a direction that intersects the direction of transport. These aspects similarly apply to the margin welded portion pairs jyP in the margin portion 31out (41out) as well.

Figure 10:
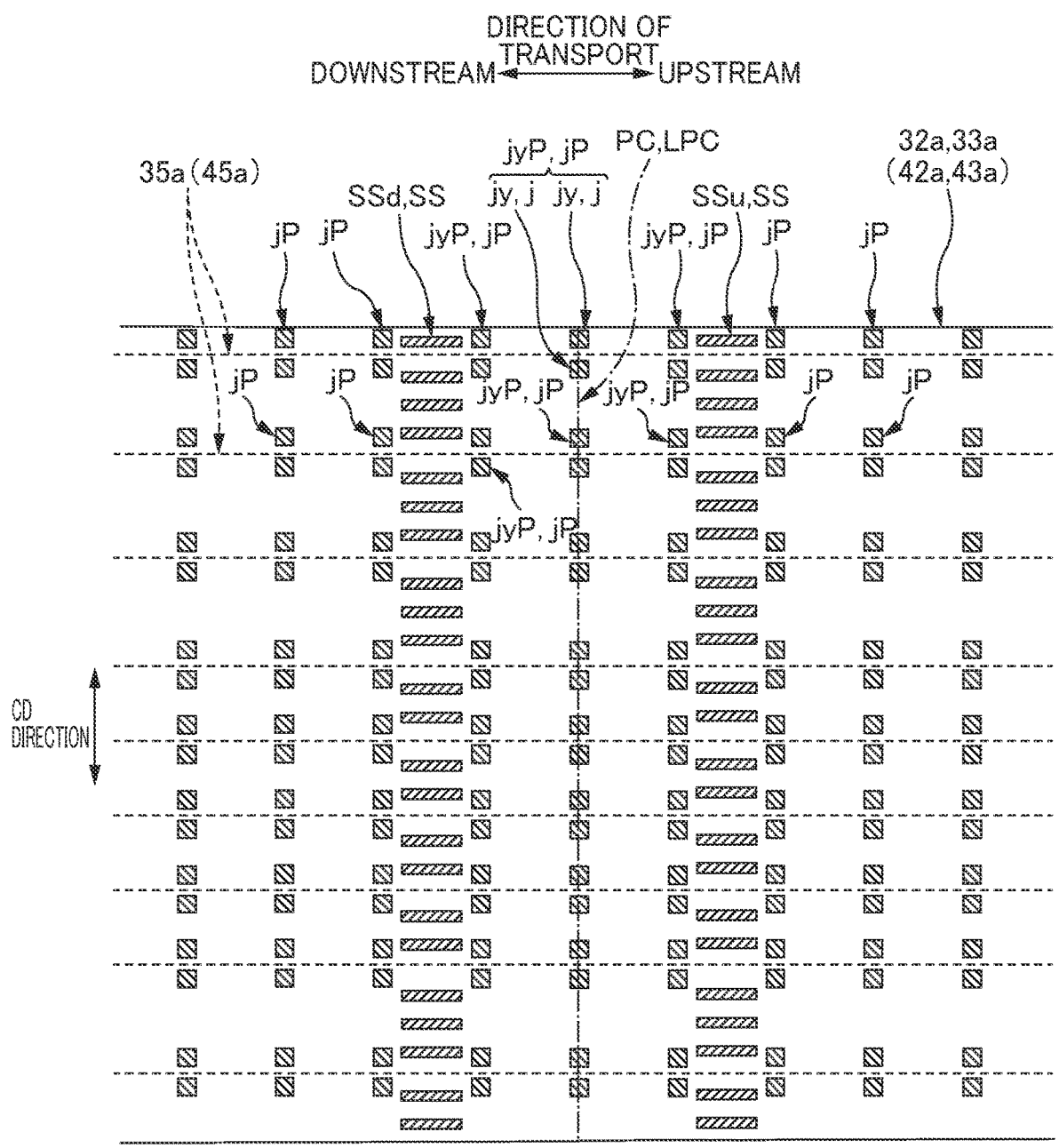
FIG. 10 is a schematic illustrative diagram of an example in which a margin welded portion jy is provided straddling a cutting target line LPC.

Also, in the example in FIG. 10, a straight cutting target line LPC that extends in the CD direction is set as the cutting target position PC. Accordingly, cutting is performed at the cutting target line LPC in the previously described cutting step. Here, in this example, at least one (e.g., several) of the margin welded portions jy, jy . . . is provided straddling the cutting target line LPC in the direction of transport.

Accordingly, after cutting is performed at the cutting target line LPC, the margin welded portions jy can suppress cases where the pair of facing surfaces of the nonwoven fabric sheets 32 and 33 (42 and 43) of the band members 31 (41) of the diaper 1 spread apart so as to form an opening, thus degrading the appearance.

Note that in the example in FIG. 10, all of the welded portions j, j . . . have an approximately square planar shape, and therefore the margin welded portions jy also have an approximately square planar shape, but there is no limitation whatsoever to this. For example, given that the margin welded portions jy are provided so as to straddle the cutting target line LPC in the direction of transport as described above, a configuration is possible in which the margin welded portions jy have a planar shape that is elongated in the longitudinal direction as in the example in FIG. 11, and the longitudinal direction intersects the direction in which the cutting target line LPC extends. Specifically, in this example, the cutting target line LPC extends in the CD direction, and the margin welded portions jy have a planar shape that is rectangular, with the longitudinal direction extending in the direction of transport. According to this configuration, it is possible to raise the probability that the margin welded portions jy will be provided straddling the cutting target line LPC in the direction of transport. Note that the planar shape that is elongated in the longitudinal direction is not limited in any way to being the above-described rectangular shape. For example, the planar shape may be a parallelogram having long sides that extend in the direction of transport, or may be an oval shape. The aforementioned probability can be raised in these cases as well.

Figure 11:
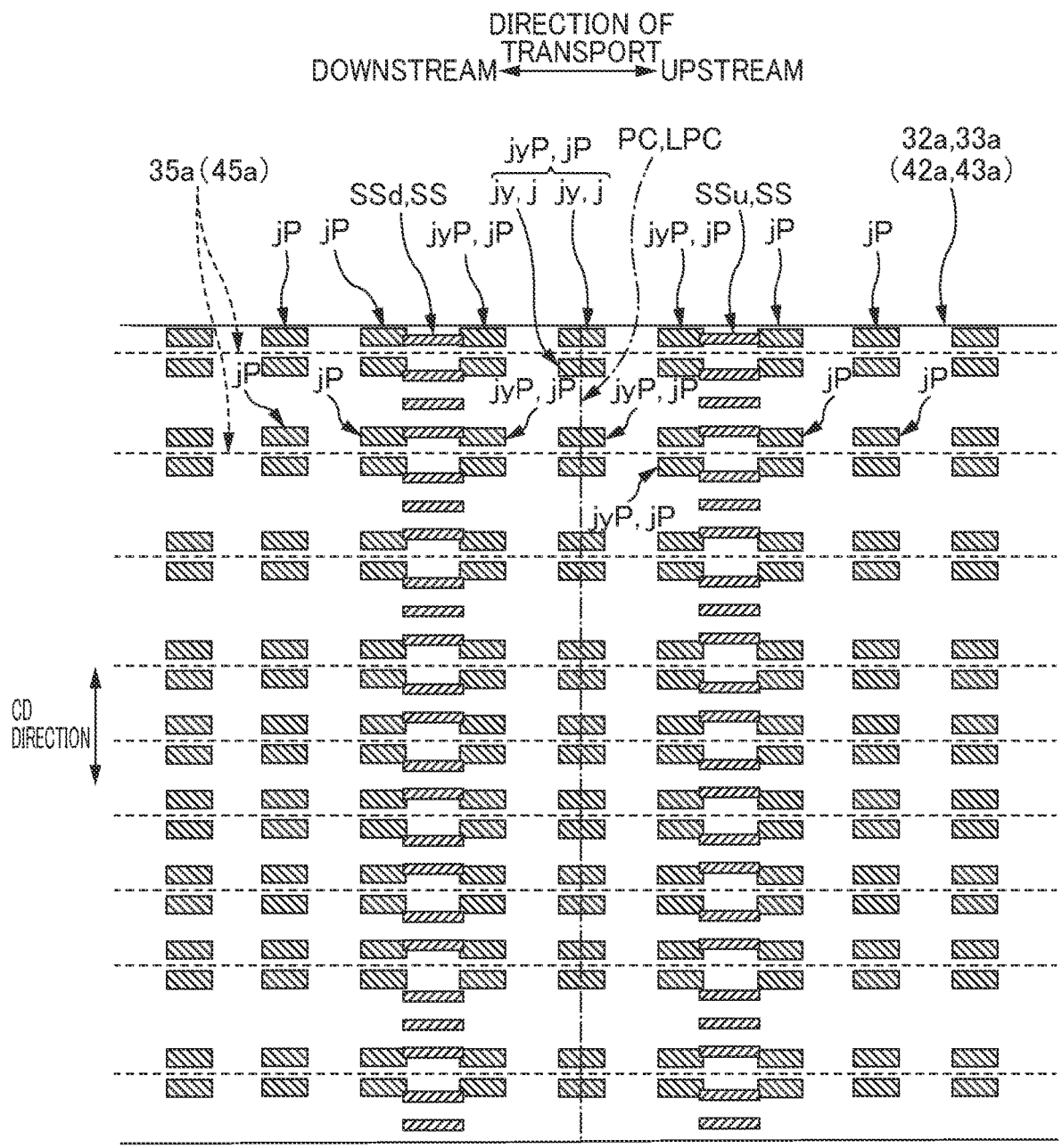
FIG. 11 is a schematic illustrative diagram of an example in which the longitudinal direction of the margin welded portion jy intersects the direction in which the cutting target line LPC extends.

Also, although all of the margin welded portions jy, jy . . . have a planar shape that is elongated in the longitudinal direction in the example in FIG. 11, there is no limitation whatsoever to this. As long as at least one of the margin welded portions jy has the above-described planar shape, it is possible to suitably achieve the effect of raising the aforementioned probability. For this reason, all of the margin welded portions jy are not required to have the above-described planar shape. For example, one-third or more, half or more, or two-thirds or more of the margin welded portions jy, jy . . . have the above-described planar shape.

Figure 12:
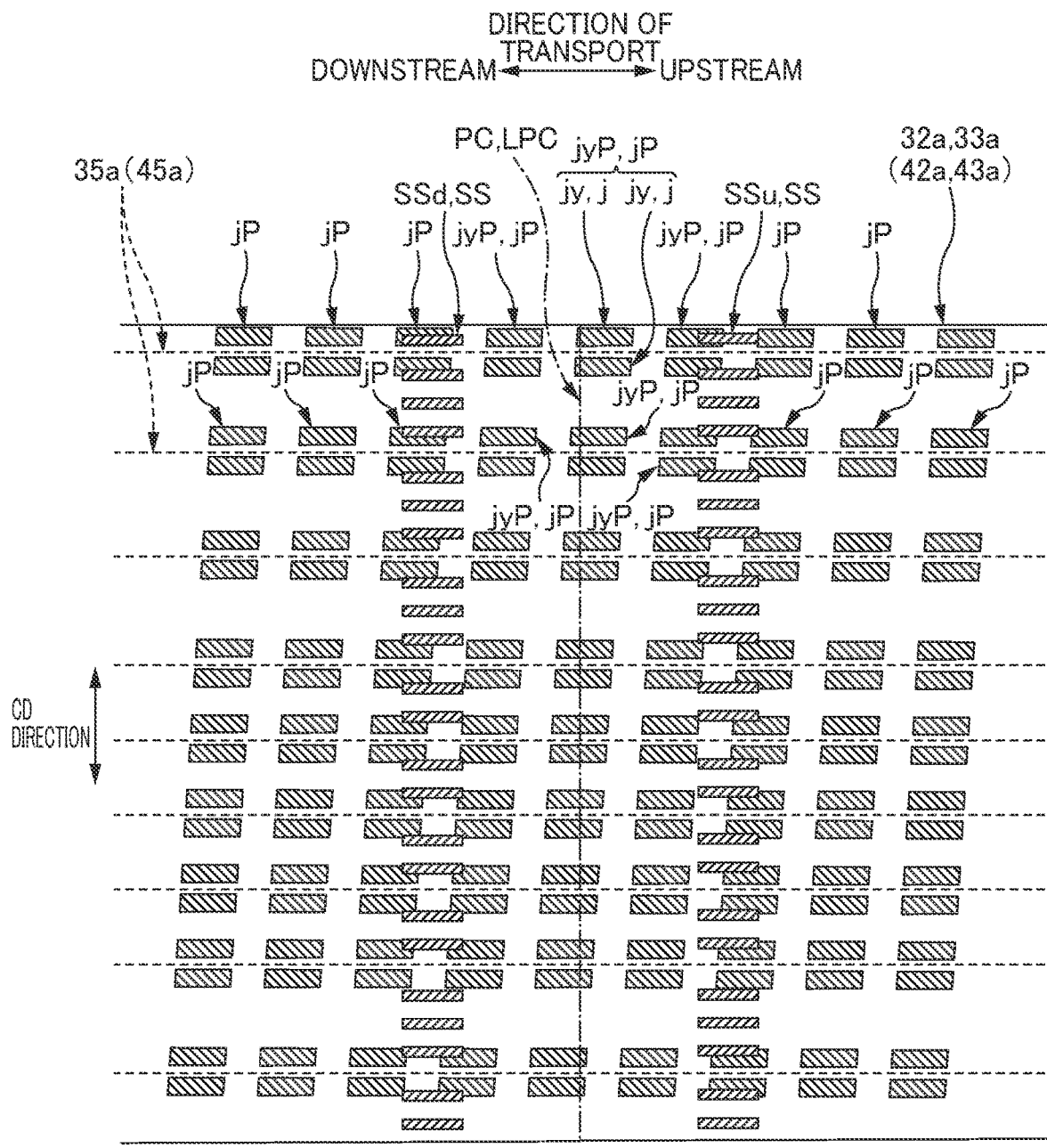
FIG. 12 is a schematic illustrative diagram of an example in which the positions of two margin welded portions jy that make up a margin welded portion pair jyP are shifted from each other in the direction of transport.

Furthermore, although the two margin welded portions jy that make up the margin welded portion pairs jyP are provided at the same position as each other in the direction of transport in the example in FIG. 11, there is no limitation whatsoever to this. For example, as shown in FIG. 12, the positions of the two margin welded portions jy may be shifted from each other in the direction of transport (lateral direction) as long as the elastic string 35 (45) be can sandwiched and pressed therebetween. According to this configuration, it is possible to further raise the aforementioned probability. Also, as shown in FIG. 12, the margin welded portions jy, jy . . . may be located on a virtual line that intersects the direction of transport as previously described. Note that in this example, the virtual line extends in a direction that is inclined from the CD direction. Also, as shown in FIG. 12, the above configurations may be applied to welded portion pairs jP other than the margin welded portion pairs jyP, that is to say the welded portion pairs jP that are not formed at the position P31out (P41out) corresponding to the margin portion 31out (41out). Specifically, the two welded portions j that make up the aforementioned welded portion pair jP may be located at positions that are shifted from each other in the direction of transport (lateral direction), and the welded portions j may be located on the aforementioned virtual line. Also, although FIG. 12 illustrates an example in which the welded portions j (including the margin welded portions jy) have an approximately parallelogram planar shape as described in the above example, there is no limitation whatsoever to this.

The welded portions j (including the margin welded portions jy) can be formed using a heat sealing device or an ultrasonic sealing device (corresponding to a joining-portion forming device) that is not shown, for example. A heat sealing device has a pair of rolls that are heated while rotating in the direction of transport, for example. One of the rolls is a heat emboss roll that has protrusion portions corresponding to the welded portions j on the outer circumferential surface, and the other roll is an anvil roll that receives the protrusion portions with a smooth outer circumferential surface. Also, an ultrasonic sealing device has a horn that has a vibrating surface that vibrates in a normal direction, and an anvil roll that rotates in the direction of transport, for example. The anvil roll has protrusion portions that correspond to the welded portions j on the outer circumferential surface in order to receive the vibrating surface.

The arrangement of the margin welded portions jy and the side-seal sections SS in the positional relationships shown in FIGS. 9 to 12 can be realized by setting the arrangement pattern of protrusion portions on the outer circumferential surface of a roll of the previously-described heat sealing apparatus or ultrasonic sealing apparatus, and setting the arrangement pattern of protrusion portions on the outer circumferential surface of a roll of the later-described heat sealing apparatus or ultrasonic sealing apparatus provided at fourth processing position PK4, for example.

Next, as shown in FIG. 7, the two continuous sheets 32a and 33a pertaining to the front band member 31 and the two continuous sheets 42a and 43a pertaining to the back band member 41 all pass the second processing position PK2. At this time, the single-cut absorbent main body 10 produced in a separate step (not shown) is fixed in a state of spanning between the two continuous sheets 32a and 33a pertaining to the front band member 31 and the two continuous sheets 42a and 43a pertaining to the back band member 41, thus forming the approximately ladder-shaped diaper continuous body lhs in which approximately H-shaped unfolded diapers 1h, 1h . . . are continuous with each other.

The absorbent main body 10 is fixed using a rotating drum device that is not shown, for example. The rotating drum device has a rotating drum that rotates in the direction of transport, and the rotating drum has a plurality of holding portions that detachably hold the absorbent main body 10 to the outer circumferential surface, for example.

Next, the approximately ladder-shaped diaper continuous body 1hs passes the third processing position PK3. At this time, the absorbent main body 10 is folded one time at a predetermined position CL1 in the CD direction, and therefore the two continuous sheets 32a and 33a pertaining to the front band member 31 and the two continuous sheets 42a and 43a pertaining to the back band member 41 are overlaid on each other in the thickness direction (corresponding to an overlaying step).

The folding can be performed using a fold guiding device (corresponding to an overlaying device) that is not shown, for example. The fold guiding device has a guide plate and guide rollers that are arranged at predetermined positions in the direction of transport, for example. The guide plate and the guide rollers guide the approximately ladder-shaped diaper continuous body lhs passing at the arrangement position so as to be folded one time.

Next, the folded diaper continuous body 1hsb passes the fourth processing position PK4. At this time, concerning the two continuous sheets 32a and 33a pertaining to the front band member 31 and concerning the two continuous sheets 42a and 43a pertaining to the back band member 41, the continuous sheets 32a and 33a and 42a and 43a which are overlaid in the thickness direction are welded at positions on two sides of the cutting target position PC in the direction of transport so as to form a pair of side-seal sections SS (corresponding to a side-seal-section forming step), thus fixing the diaper continuous body 1hsb in the folded state. This consequently produces an underpants-shaped diaper continuous body is in which a plurality of underpants-shaped diapers 1, 1 . . . are connected in the lateral direction.

Here, given that the CD direction conforms to the vertical direction of the diaper 1, as shown in FIG. 8C, the side-seal sections SS have a plurality of welded portions SSk, SSk . . . that are side-by-side in the CD direction (vertical direction). The welded portions SSk weld together the continuous sheet 33a of the front band member 31 and the continuous sheet 43a of the back band member 41, weld together the pair of facing surfaces of the continuous sheets 32a and 33a of the front band member 31, and weld together the pair of facing surfaces of the continuous sheets 42a and 43a of the back band member 41 (FIG. 7).

Also, in this example in FIGS. 8C and 9, the planar shape of the welded portions SSk is a laterally elongated rectangular shape that is longer in the lateral direction, which is the CD direction, than in the vertical direction, which is the direction of transport. Note that there is no limitation whatsoever to this. For example, it may have a parallelogram shape or oval shape, or may have another shape. Also, in this example, the longitudinal direction of the welded portions SSk conforms to the lateral direction, which is the direction of transport, but there is no limitation whatsoever to this. In other words, the longitudinal direction of the welded portions SSk may conform to the vertical direction, which is the CD direction, or may conform to a direction that intersects both the lateral direction and the vertical direction.

Furthermore, in the example in FIG. 9, when the direction-of-transport size LSSPC at the position P31out (P41out) corresponding to the margin portion 31out (41out), that is to say the size LSSPC of the direction-of-transport space between the side-seal section SS and the cutting target position PC, is compared with the direction-of-transport size LSS of the side-seal section SS at the fourth processing position PK4, the former size LSSPC is greater than the latter size LSS.

Accordingly, a larger space LSSPC can be ensured between the side-seal section SS and the cutting target position PC more easily than in the case where the size relationship is the opposite of the above-described relationship. This makes it possible to more easily ensure a relatively large distance in the direction of transport between the margin welded portions jy and the portions 35ae that will be the end portions of the 35e of the elastic strings 35 in the elastic-string continuous bodies 35a. With this configuration, the elastic strings 35 can contract in the direction of transport so as to swiftly expand in the CD direction such that the elastic strings 35 35 can be sandwiched and pressed between the pairs of margin welded portions jy. As a result, it is possible to suppress the detachment of the end portions 35e of the elastic strings 35 from the margin welded portions jy.

It should be noted that the direction-of-transport size LSS of the side-seal section SS and the direction-of-transport size LSSPC of the space between the side-seal section SS and the cutting target position PC are defined as previously described.

The side-seal sections SS can be formed using a heat sealing device or an ultrasonic sealing device (corresponding to a side-seal-section forming device) that is not shown, for example. A heat sealing device has a pair of rolls that are heated while rotating in the direction of transport, for example. One of the rolls is a heat emboss roll that has protrusion portions corresponding to the welded portions SSk of the side-seal sections SS on the outer circumferential surface, and the other roll is an anvil roll that receives the protrusion portions with a smooth outer circumferential surface. Also, an ultrasonic sealing device has a horn that has a vibrating surface that vibrates in a normal direction, and an anvil roll that rotates in the direction of transport, for example. The anvil roll has protrusion portions that correspond to the welded portions SSk on the outer circumferential surface in order to receive the vibrating surface.

Next, as shown in FIG. 7, the underpants-shaped diaper continuous body is passes the fifth processing position PK5. At this time, the continuous body 1s is cut at the cutting target position PC that is located between a pair of side-seal sections SS (corresponding to a cutting step), thus obtaining the diaper 1.

Note that at the time of this cutting, the two continuous sheets 32a and 33a (42a and 43a) pertaining to the front band member 31 and the back band member 41 and the elastic-string continuous bodies 35a, 35a . . . (45a, 45a . . . ) are cut at the cutting target position PC. Due to the corresponding relaxation of the stretched state of the elastic strings 35 (45), the elastic strings 35 (45) are sandwiched and pressed by the pairs of welded portions j in the welded portion pairs jP and are thus attached to the band members 31 and 41, and this is the same as in the description of the first processing position PK1.

This cutting can be performed using a cutter device (corresponding to a cutting device) that is not shown, for example. A cutter device has a pair of rolls that rotate in the direction of transport, for example. One of the rolls is a cutter roll that has a cutter blade on the outer circumferential surface, and the other roll is an anvil roll having an outer circumferential surface that receives the cutter blade.

Figure 13:
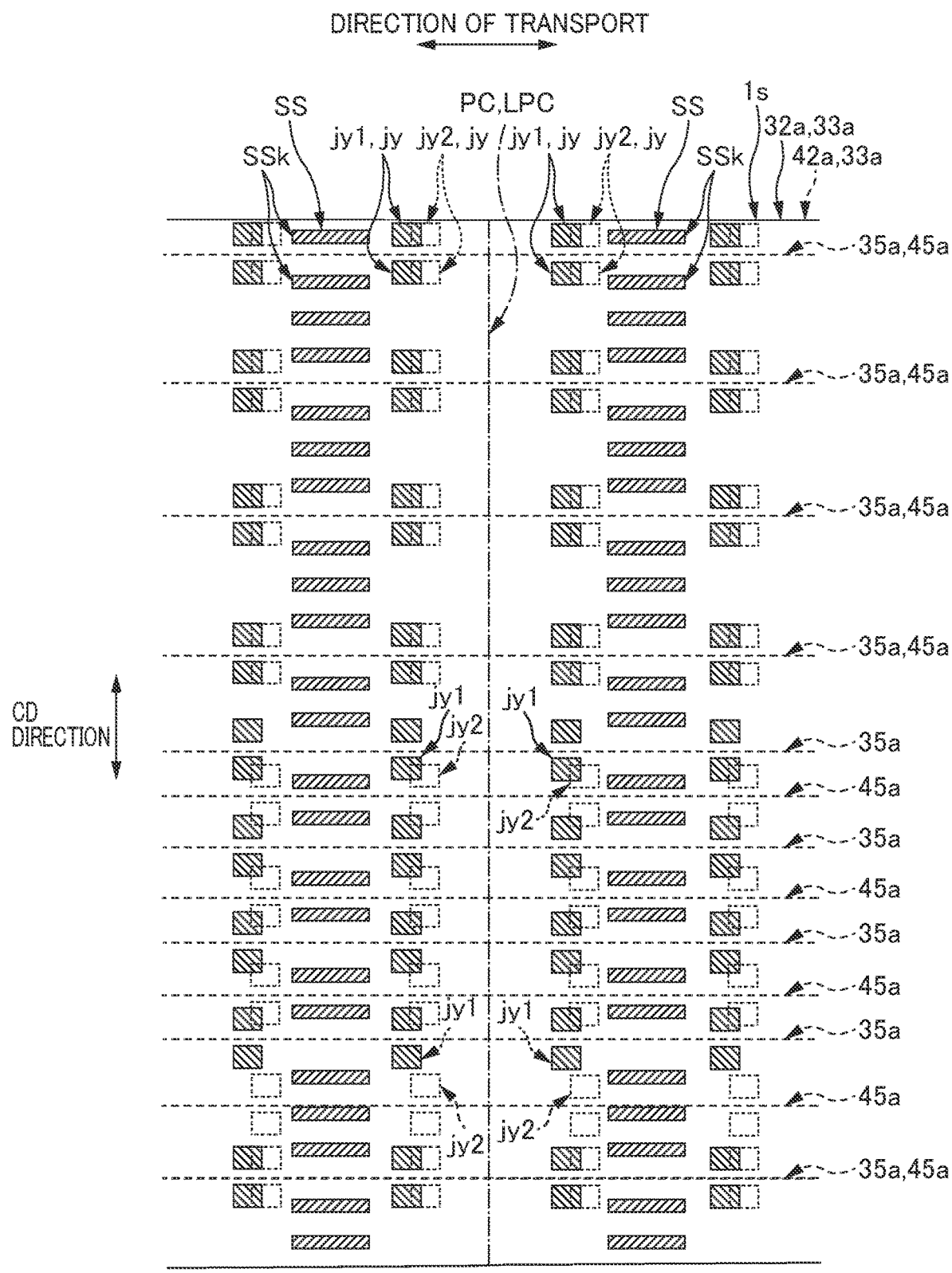
FIG. 13 is a schematic illustrative view of a positional relationship between margin welded portions jy of the continuous sheets 32a and 33a pertaining to the front band member 31 and margin welded portions jy of the continuous sheets 42a and 43a pertaining to the back band member 41.

FIG. 13 is a schematic illustrative view of a positional relationship between margin welded portions jy of the continuous sheets 32a and 33a pertaining to the front band member 31 and margin welded portions jy of the continuous sheets 42a and 43a pertaining to the back band member 41. Specifically, FIG. 13 is a schematic plan view of the underpants-shaped-disposable-diaper continuous body is that is transported between the fourth processing position PK4 and the fifth processing position PK5 in the manufacturing line (FIG. 7). More specifically, it is a schematic view of the cutting target position PC and the vicinity thereof in the continuous body is as viewed from the front band member 31 side in the thickness direction.

As shown in FIG. 13, first, the elastic-string continuous bodies 35a of the front band member 31 and the elastic-string continuous bodies 45a of the back band member 41 are overlapped in the thickness direction at several locations in the CD direction, whereas at several other locations, there are only the elastic-string continuous bodies 35a of the front band member 31, and at still other locations there are only the elastic-string continuous bodies 45a of the back band member 41 are provided.

Also, here, letting the margin welded portions jy formed in the continuous sheets 32a and 33a pertaining to the front band member 31 be called "first margin welded portions jy1" (corresponding to first margin joining portions), and letting the margin welded portions jy formed in the continuous sheets 42a and 43a pertaining to the back band member 41 be called "second margin welded portions jy2" (corresponding to second margin joining portions), in this example, all of the first margin welded portions jy1 are shifted in the direction of transport or the CD direction with respect to the second margin welded portions jy2 that are closest to the first margin welded portions jy1. Specifically, in this example, all of the first margin welded portions jy1, jy1 . . . are shifted in the direction of transport with respect to the second margin welded portions jy2 that are closest thereto. Also, several of the first margin welded portions jy1, jy1 . . . are shifted in the CD direction as well with respect to the corresponding second margin welded portions jy2, and several of those first margin welded portions jy1 are shifted not being overlapped at all with the corresponding second margin welded portions jy2.

According to this configuration of one or more embodiments, it is possible to suppress stiffness that can occur if the first margin welded portions jy1 and the second margin welded portions jy2 are completely overlapped, that is to say the stiffness of the margin portion 31out (41out), which is located laterally outward with respect to the side-seal sections SS of the diaper 1 will vary greatly, which is likely to cause the person touching those portions to feel discomfort.

Note that there is no limitation whatsoever to this. Specifically, it is possible to suitably achieve the above-described effect of suppressing variation in stiffness as long as at least one, one-third or more, half or more, or two-thirds or more of all of the first margin welded portions jy1, jy1 . . . are shifted in the direction of transport or the CD direction with respect to the closest second margin welded portion jy2. Also, the shifted first margin welded portion jy1 does not need to be shifted in both the direction of transport and the CD direction. In other words, the first margin welded portion jy1 may be shifted in the direction of transport and not in the CD direction, or conversely, may be shifted in the CD direction and not in the direction of transport, and such first margin welded portions jy1 are also shown in the example in FIG. 13.

Also, the above-described CD-direction shifting of the first margin welded portion jy1 can be realized by adjusting in the CD direction the folding position at which the approximately ladder-shaped diaper continuous body 1hs is folded at the third processing position PK3; the folding position is a predetermined position in the CD direction. Specifically, adjusting the predetermined position in the CD direction causes to adjust the relative positions in the CD direction of the for-back-band-member-41 continuous sheets 42a and 43a relative to the for-front-band-member-31 continuous sheets 32a and 33a, and this makes it possible to reliably achieve the aforementioned positional shifting.

Furthermore, the above-described direction-of-transport shifting of the first margin welded portion jy1 can be realized by adjusting the rotation-direction phases of the following rolls: the first one is a roll of the previously described heat sealing device or ultrasonic sealing device arranged at the first processing position PK1, and has protrusions;

and the second one is a roll of the previously described heat sealing device or ultrasonic sealing device arranged at the fourth processing position PK4, and has protrusions.

Although embodiments of the present disclosure have been described hereinabove, the above embodiments of the present disclosure are simply for facilitating understanding of the present disclosure and are not in any way to be construed as limiting the present disclosure. The present disclosure may variously be changed or altered without departing from its gist and encompass equivalents thereof. For example, modification which will be described below is possible.

In the above embodiments, the welded portion j is illustrated as an example of the joining portion (second joining portion) that joins together the mutually-opposing pair of facing surfaces of the two nonwoven fabric sheets 32 and 33 (42 and 43) as shown in FIG. 5, but there is no limitation whatsoever to this. For example, according to one or more embodiments, the joining portion (second joining portion) may be formed using an adhesive, and in this case, the adhesive is selectively applied, on at least one of the two facing surfaces, to a target formation position at which the joining portion (second joining portion) is to be formed.

In the above embodiments, two continuous sheets 32a and 33a (42a and 43a) are illustrated as examples of the first sheet-like-member continuous body (second sheet-like-member continuous body) as shown in FIG. 7, but there is no limitation whatsoever to this. For example, according to one or more embodiments, the first sheet-like-member continuous body (second sheet-like-member continuous body) may be constituted by one continuous sheet. In this case, the pair of facing surfaces are formed by folding one continuous sheet at a predetermined position in the CD direction, and then inserting the elastic-string continuous bodies 35a (45a) between the pair of facing surfaces.

In the above embodiments, the elastic strings 35 (45) are illustrated as examples of elastic members (second elastic members), and the elastic-string continuous bodies 35a (45a) are illustrated as examples of the elastic-member continuous bodies (continuous bodies of the second elastic member), but according to one or more embodiments spandex and the like are other specific examples of such elastic strings 35 (45), and LYCRA (registered trademark) is an example of such a product. Also, according to one or more embodiments, the elastic strings 35 (45) can have a fiber density of 400 dtex to 1,000 dtex, for example. Furthermore, rubber strips may be used as the elastic members (second elastic members), and rubber strip continuous bodies may be used as the elastic-member continuous bodies (second elastic-member continuous bodies).

In the above embodiments, as shown in FIG. 5, all of the elastic strings 35, 35 . . . provided in the front band member 31 are arranged so as to be continuous over substantially the entire length in the lateral direction, but there is no limitation whatsoever to this. For example, according to one or more embodiments, several of the elastic strings 35, 35 . . . may be discontinuous at a central position in the lateral direction for example. Note that the same applies to the elastic strings 45, 45 . . . of the back band member 41 as well.

In the above embodiments, as shown in FIG. 3, the three-piece type of disposable diaper 1 is illustrated as an example of the absorbent article, but there is no limitation whatsoever to this. For example, the method of one or more embodiments of the present invention may be used when attaching elastic members such as elastic strings to a sheet-like member for use in a two-piece type of disposable diaper. A two-piece type disposable diaper is a type of diaper that has a first component and a second component: the first component is an exterior sheet having a two-layer structure and including a front portion, a crotch portion, and a back portion; and the second component is the absorbent main body 10 fixed to the skin-side surface of the exterior sheet.

In the above embodiments, as shown in FIG. 5, the welded portions j, j . . . are provided in a so-called ladder-like arrangement that is defined in the lateral direction and the vertical direction (longitudinal direction). Specifically, the welded portions j, j . . . are provided at intersections between virtual lines extending in the lateral direction and virtual lines extending in the vertical direction, but there is no limitation whatsoever to this. For example, according to one or more embodiments, the welded portions j, j . . . may be provided in a so-called staggered arrangement by being providing at positions that are shifted in the lateral direction from the aforementioned intersections. Also, although the welded portions j, j . . . are arranged side-by-side in the vertical direction in FIG. 5, there is no limitation whatsoever to this. For example, the welded portions j, j . . . may be arranged side-by-side in a diagonal direction that intersects both the vertical direction and the lateral direction.

In the above embodiments, as shown in FIG. 5, a welded portion j is not provided between two welded portion pairs jP that are adjacent in the vertical direction (CD direction), but there is no limitation whatsoever to this. For example, according to one or more embodiments, one or more welded portions j may be provided between two welded portion pairs jP. Note that such a welded portion j does not contribute to attachment of the elastic strings 35 (45) to the nonwoven fabric sheets 32 and 33 (42 and 43), and only contributes to the joining of the nonwoven fabric sheets 32 and 33 (42 and 43) to each other.

In the above embodiments, the elastic strings 35 (45) attempt to contract in the direction of transport and expand in the CD direction due to the cutting performed in the cutting step at the fifth processing position PK5, but are sandwiched and pressed in the CD direction between pairs of welded portions j, and the elastic strings 35 (45) are thus attached to the two nonwoven fabric sheets 32 and 33 (42 and 43). However, there is no limitation whatsoever to this. Specifically, according to one or more embodiments, a configuration is possible in which, at a stage before the cutting step, the elastic-string continuous bodies 35a (45a), which have been inserted between the pair of facing surfaces of the continuous sheets 32a and 33a (42a and 43a) pertaining to the two nonwoven fabric sheets 32 and 33 (42 and 43), are allowed to relax from the stretched state such that the continuous bodies 35a (45a) contract in the direction of transport, and thus the continuous bodies 35a (45a) are sandwiched and pressed in the CD direction between the pair of welded portions j. For example, a configuration is possible in which the elastic-string continuous bodies 35a (45a) in the underpants-shaped diaper continuous body is in FIG. 8 are allowed to relax from the stretched state such that the continuous bodies 35a (45a) contract in the direction of transport, and thus the continuous bodies 35a (45a) are sandwiched and pressed in the CD direction between the pair of welded portions j. Subsequently, the underpants-shaped diaper continuous body is may be cut in the cutting step, thus producing the diaper 1.

In the above embodiments, in addition to the nonwoven fabric sheets 32 and 33 that are to be produced by cutting the two continuous sheets 32a and 33a (an example of the first sheet-like-member continuous body), the nonwoven fabric sheets 42 and 43 that are produced by cutting the two continuous sheets 42a and 43a (an example of the second sheet-like-member continuous body) also include the elastic strings 45 (the second elastic members) attached thereto by being sandwiched and pressed between pair of welded portions j (second joining portions). However, there is no limitation whatsoever to this. In other words, in the nonwoven fabric sheets 42 and 43, the elastic strings 45 may be attached by not only being sandwiched and pressed between pairs of welded portions j, but also by the adhesive. Also, according to one or more embodiments, in the nonwoven fabric sheets 42 and 43, the margin welded portions jy are not required to be provided, that is to say, the second elastic members such as the elastic strings 45 can also be omitted from the nonwoven fabric sheets 42 and 43.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST 1 disposable diaper (absorbent article),
1*hs* approximately ladder-shaped diaper continuous body,
1*hsb* folded diaper continuous body,
1*s* underpants-shaped diaper continuous body,
10 absorbent main body, 10*ea* end portion, 10*eb* end portion,
11 absorbent body, 11*c* absorbent core,
13 top sheet, 15 back sheet,
17 elastic string (elastic member), 18 elastic string (elastic member),
31 front band member, 31*e* end portion,
31in inward portion,
31out margin portion (outward portion),
32 nonwoven fabric sheet, 32*a* continuous sheet,
33 nonwoven fabric sheet, 33*a* continuous sheet,
35 elastic string (elastic member), 35*e* end portion,
35*a* elastic-string continuous body (elastic-member continuous body),
35*ae* portion,
41 back band member, 41*e* end portion,
41in inward portion,
41out margin portion (outward portion),
42 nonwoven fabric sheet, 42*a* continuous sheet,
43 nonwoven fabric sheet, 43*a* continuous sheet,
45 elastic string (second elastic member), 45*e* end portion,
45*a* elastic-string continuous body (second elastic-member continuous body),
BH waist opening, LH leg opening,
LG leg gather, LSG barrier cuff,
j welded portion (joining portion, second joining portion),
jy margin welded portion (joining portion, second welded portion),
jy1 first margin welded portion (first margin joining portion),
jy2 second margin welded portion (second margin joining portion),
jP welded portion pair (joining portion pair), jyP margin welded portion pair (joining portion pair), SS side-seal section,
SSd downstream side-seal section, SSdeu upstream end,
SSu upstream side-seal section, SSued downstream end,
SSk welded portion, SSkeu upstream end, SSked downstream end,
NSS side-seal-portion-non-formation portion,
CL1 central position (predetermined position)
PC cutting target position, LPC cutting target line, PBL boundary position,
PK1 first processing position, PK2 second processing position, PK3 third processing position,
PK4 fourth processing position, PK5 fifth processing position

What is claimed is:

1. An absorbent article comprising:
a first sheet;
a second sheet;
an elastic member that is inserted along a lateral direction between a pair of mutually-opposing facing surfaces of the first sheet;
joining portions that join the pair of mutually-opposing facing surfaces and that are spaced apart in the lateral direction, wherein
the joining portions are disposed on two sides of the elastic member in a vertical direction, which intersects the lateral direction and a front-rear direction, so that the elastic member is sandwiched and pressed between the joining portions; and
side-seal sections that are disposed at each lateral end portion of the absorbent article, wherein
a portion of at least one of the joining portions is disposed laterally outward of the side-seal sections in a thickness of the first sheet,
the first sheet and the second sheet are overlaid in the front-rear direction and welded in the side-seal section, and
a longitudinal direction of at least one of the joining portions that is located between the side-seal section and a side edge in the lateral direction intersects a direction in which the side edge extends.

2. A method for manufacturing an absorbent article that comprises a first sheet, a second sheet, a first elastic member, and side-seal sections, wherein the first elastic member is attached to the first sheet, the first sheet is stretchable in a lateral direction using the first elastic member, the side-seal sections are disposed at each lateral end portion of the absorbent article, the first sheet and the second sheet are overlaid in a thickness direction and welded together at the side-seal sections, and the thickness direction intersects the lateral direction, the method comprising:
arranging first elastic-member continuous bodies between a pair of mutually-opposing facing surfaces of a first sheet continuous body that is transported in a transport direction that is the same as the lateral direction, wherein
the first elastic-member continuous bodies and the first sheet continuous body are arranged continuously in the transport direction, and
the first elastic-member continuous bodies are in a stretched state in the transport direction;
disposing first joining portions spaced apart in the transport direction on the first sheet continuous body, wherein
the first joining portions join the pair of mutually-opposing facing surfaces,
the first joining portions are disposed on two sides of the first elastic-member continuous bodies in a CD direction that intersects the transport direction and the thickness direction while maintaining the first elastic-member continuous bodies in the stretched state,
the first joining portions are disposed so that, by direction-of-transport contraction and CD-direction expansion of the first elastic member after cutting of the absorbent article, the first elastic member is sandwiched and pressed in the CD direction by the first joining portions on the two sides of the first elastic-member continuous bodies,
the first joining portions are disposed so that a portion of at least one of the first joining portions is in the transport direction between the side-seal sections and each cutting target position in a thickness direction of the first sheet continuous body, and
the cutting target positions are set at a predetermined pitch in the transport direction;
overlaying, in the thickness direction, a second sheet continuous body on the first sheet continuous body where the first joining portions are disposed, wherein the second sheet continuous body is arranged continuously in the transport direction;
disposing, in the transport direction, the side-seal sections on each of two sides of the cutting target positions, wherein the first sheet continuous body and the second sheet continuous body are welded together at the side-seal sections; and
the cutting of the absorbent article, after the disposing of the side-seal sections, by cutting the first sheet continuous body, the first elastic-member continuous bodies, and the second sheet continuous body at the cutting target positions, wherein
the absorbent article is cut along cutting target lines that serve as the cutting target positions and that extend in the CD direction, and
a longitudinal direction of at least one of the first joining portions that is located between the side-seal sections and one of the cutting target lines intersects a direction in which the cutting target lines extend.

3. The method according to claim 1, wherein the at least one of the first joining portions straddles the cutting target lines in the transport direction.

4. The method for manufacturing an absorbent article according to claim 1, wherein
the first elastic-member continuous bodies are arranged side-by-side in the CD direction,
first joining portion pairs each comprising two of the first joining portions that are on the two sides of the first elastic-member continuous bodies in the CD direction are disposed for each of the first elastic-member continuous bodies, and
at least three of the first joining portion pairs, disposed between the side-seal sections and one of the cutting target positions, are disposed in a straight line that intersects the transport direction.

5. The method according to claim 1, wherein
the first joining portions are disposed at a predetermined formation pitch in the transport direction to span and extend in the transport direction beyond one of the cutting target positions and beyond the side-seal sections on the two sides of the one of the cutting target positions, and
the predetermined formation pitch is smaller than half of a direction-of-transport size of a side-seal-portion-non-formation portion comprising a portion of the first sheet continuous body between the side-seal sections on the two sides of the one of the cutting target positions without the side-seal sections.

6. The method according to claim 1, wherein
a second elastic member is attached to the second sheet,
the second sheet is stretchable in the lateral direction using the second elastic member,
the method further comprises:
   arranging second elastic-member continuous bodies between a pair of mutually-opposing facing surfaces of the second sheet continuous body, wherein the second elastic-member continuous bodies are arranged continuously and in the stretched state;
   disposing second joining portions spaced apart in the transport direction on the second sheet continuous body, wherein
      the second joining portions join the pair of mutually-opposing facing surfaces of the second sheet continuous body,
      the second joining portions are disposed on two sides of the second elastic-member continuous bodies in the CD direction while maintaining the second elastic-member continuous bodies in the stretched state,
      the second joining portions are disposed so that, by direction-of-transport contraction and CD-direction expansion of the second elastic member after the cutting of the absorbent article, the second elastic member is sandwiched and pressed in the CD direction by the second joining portions on the two sides of the second elastic-member continuous bodies, and
      the second joining portions are disposed so that a portion of at least one of the second joining portions is in the transport direction between the side-seal sections and each of the cutting target positions in the thickness direction of the second sheet continuous body;
   in the overlaying of the second sheet continuous body on the first sheet continuous body, overlaying the second joining portions on the first joining portions; and
   in the cutting of the absorbent article, cutting the first sheet continuous body, the first elastic-member continuous bodies, the second sheet continuous body, and the second elastic-member continuous bodies at each of the cutting target positions.

7. The method according to claim 6, wherein
the first sheet continuous body and the second sheet continuous body are overlaid such that a first margin joining portion is shifted in the transport direction or the CD direction with respect to a second margin joining portion that is closest to the first margin joining portion,
the first margin joining portion comprises one of the first joining portions that is partially disposed between the side-seal sections and one of the cutting target positions, and
the second margin joining portion comprises one of the second joining portions that is partially disposed between the side-seal sections and one of the cutting target positions.

8. A device for manufacturing an absorbent article that includes a first sheet, a second sheet, an elastic member, and side-seal sections, wherein the elastic member is attached to the first sheet, the first sheet is stretchable in a lateral direction using the elastic member, the side-seal sections are disposed at each lateral end portion of the absorbent article, the first sheet and the second sheet are overlaid in a thickness direction and welded together at the side-seal sections, and the thickness direction intersects the lateral direction, the device comprising:
   an arranging device that arranges elastic-member continuous bodies between a pair of mutually-opposing facing surfaces of a first sheet continuous body that is transported in a transport direction that is the same as the lateral direction, wherein
      the elastic-member continuous bodies and the first sheet continuous body are arranged continuously in the transport direction, and
      the elastic-member continuous bodies are in a stretched state in the transport direction;
   a joining-portion forming device that disposes joining portions spaced apart in the transport direction on the first sheet continuous body, wherein
      the joining portions join the pair of mutually-opposing facing surfaces,
      the joining portions are disposed on two sides of the elastic-member continuous bodies in a CD direction that intersects the transport direction while maintaining the elastic-member continuous bodies in the stretched state,
      the joining portions are disposed so that, by direction-of-transport contraction and CD-direction expansion of the elastic member at a position downstream of the transport direction with respect to a cutting device, the elastic member is sandwiched and pressed in the CD direction by the joining portions on the two sides of the first elastic-member continuous bodies,
      the joining portions are disposed so that a portion of at least one of the joining portions is in the transport direction between the side-seal sections and each cutting target position in a thickness direction of the first sheet continuous body, and
      the cutting target positions are set at a predetermined pitch in the transport direction;
   an overlaying device that overlays, in the thickness direction, a second sheet continuous body on the first sheet continuous body where the joining portions are disposed, wherein the second sheet continuous body is arranged continuously in the transport direction;
   a side-seal-section forming device that disposes, in the transport direction, the side-seal sections on each of two sides of the cutting target positions, wherein the first sheet continuous body and the second sheet continuous body are welded together at the side-seal sections; and
   the cutting device that is disposed at the position downstream in the transport direction with respect to the side-seal-section forming device and that cuts the first sheet continuous body, the elastic-member continuous bodies, and the second sheet continuous body at the cutting target positions, wherein
   the absorbent article is cut along cutting target lines that serve as the cutting target positions and that extend in the CD direction, and
   a longitudinal direction of at least one of the first joining portions that is located between the side-seal sections and one of the cutting target lines intersects a direction in which the cutting target lines extend.

9. A device for manufacturing an absorbent article that includes a first sheet, a second sheet, an elastic member, and side-seal sections, wherein the elastic member is attached to the first sheet, the first sheet is stretchable in a lateral direction using the elastic member, the side-seal sections are disposed at each lateral end portion of the absorbent article, the first sheet and the second sheet are overlaid in a thickness direction and welded together at the side-seal sections, and the thickness direction intersects the lateral direction, the device comprising:

an arranging device that arranges elastic-member continuous bodies between a pair of mutually-opposing facing surfaces of a first sheet continuous body that is transported in a transport direction that is the same as the lateral direction, wherein
the elastic-member continuous bodies and the first sheet continuous body are arranged continuously in the transport direction, and
the elastic-member continuous bodies are in a stretched state in the transport direction;

a joining-portion forming device that disposes joining portions spaced apart in the transport direction on the first sheet continuous body, wherein
the joining portions join the pair of mutually-opposing facing surfaces,
the joining portions are disposed on two sides of the elastic-member continuous bodies in a CD direction that intersects the transport direction while maintaining the elastic-member continuous bodies in the stretched state,
the joining portions are disposed so that, by direction-of-transport contraction and CD-direction expansion of the elastic member at a position downstream of the transport direction with respect to a cutting device, the elastic member is sandwiched and pressed in the CD direction by the joining portions on the two sides of the first elastic-member continuous bodies,
the joining portions are disposed so that a portion of at least one of the joining portions is in the transport direction between the side-seal sections and each cutting target position in a thickness direction of the first sheet continuous body, and
the cutting target positions are set at a predetermined pitch in the transport direction;

an overlaying device that overlays, in the thickness direction, a second sheet continuous body on the first sheet continuous body where the joining portions are disposed, wherein the second sheet continuous body is arranged continuously in the transport direction;

a side-seal-section forming device that disposes, in the transport direction, the side-seal sections on each of two sides of the cutting target positions, wherein the first sheet continuous body and the second sheet continuous body are welded together at the side-seal sections; and the cutting device that is disposed at the position downstream in the transport direction with respect to the side-seal-section forming device and that cuts the first sheet continuous body, the elastic-member continuous bodies, and the second sheet continuous body at the cutting target positions, wherein a size of a direction-of-transport space between the side-seal sections and one of the cutting target position is greater than a direction-of-transport size of the side-seal sections.

10. An absorbent article comprising:
a first sheet;
a second sheet;
an elastic member that is inserted along a lateral direction between a pair of mutually-opposing facing surfaces of the first sheet;
joining portions that join the pair of mutually-opposing facing surfaces and that are spaced apart in the lateral direction, wherein
the joining portions are disposed on two sides of the elastic member in a vertical direction, which intersects the lateral direction and a front-rear direction, so that the elastic member is sandwiched and pressed between the joining portions; and
side-seal sections that are disposed at each lateral end portion of the absorbent article, wherein
a portion of at least one of the joining portions is disposed laterally outward of the side-seal sections in a thickness of the first sheet,
the first sheet and the second sheet are overlaid in the front-rear direction and welded in the side-seal section, and
a size of a space between the side-seal section and a side edge in the lateral direction is greater than a size of the side-seal section in the lateral direction.

11. A method for manufacturing an absorbent article that comprises a first sheet, a second sheet, a first elastic member, and side-seal sections, wherein the first elastic member is attached to the first sheet, the first sheet is stretchable in a lateral direction using the first elastic member, the side-seal sections are disposed at each lateral end portion of the absorbent article, the first sheet and the second sheet are overlaid in a thickness direction and welded together at the side-seal sections, and the thickness direction intersects the lateral direction, the method comprising:

arranging first elastic-member continuous bodies between a pair of mutually-opposing facing surfaces of a first sheet continuous body that is transported in a transport direction that is the same as the lateral direction, wherein
the first elastic-member continuous bodies and the first sheet continuous body are arranged continuously in the transport direction, and
the first elastic-member continuous bodies are in a stretched state in the transport direction;

disposing first joining portions spaced apart in the transport direction on the first sheet continuous body, wherein
the first joining portions join the pair of mutually-opposing facing surfaces,
the first joining portions are disposed on two sides of the first elastic-member continuous bodies in a CD direction that intersects the transport direction and the thickness direction while maintaining the first elastic-member continuous bodies in the stretched state,
the first joining portions are disposed so that, by direction-of-transport contraction and CD-direction expansion of the first elastic member after cutting of the absorbent article, the first elastic member is sandwiched and pressed in the CD direction by the first joining portions on the two sides of the first elastic-member continuous bodies,
the first joining portions are disposed so that a portion of at least one of the first joining portions is in the transport direction between the side-seal sections and each cutting target position in a thickness direction of the first sheet continuous body, and the cutting target positions are set at a predetermined pitch in the transport direction;

overlaying, in the thickness direction, a second sheet continuous body on the first sheet continuous body where the first joining portions are disposed, wherein the second sheet continuous body is arranged continuously in the transport direction; and disposing, in the transport direction, the side-seal sections on each of two sides of the cutting target positions, wherein the first sheet continuous body and the second sheet continuous body are welded together at the side-seal sections, wherein the cutting of the absorbent article, after the disposing of the side-seal sections, by cutting the first sheet continuous body, the first elastic-member continuous bodies, and the second sheet continuous body at the cutting target positions, and wherein a size of a direction-of-transport space between the side-seal sections and one of the cutting target position is greater than a direction-of-transport size of the side-seal sections.

\* \* \* \* \*